(12) United States Patent
Winslow et al.

(10) Patent No.: US 8,066,749 B2
(45) Date of Patent: **\*Nov. 29, 2011**

(54) IMPLANT FOR STABILIZING A BONE GRAFT DURING SPINAL FUSION

(75) Inventors: Charles J. Winslow, Walnut Creek, CA (US); Christopher Fair, Denver, CO (US); James F. Zucherman, San Francisco, CA (US); Ken Y. Hsu, San Francisco, CA (US); Steven T. Mitchell, Pleasant Hill, CA (US); Scott A. Yerby, Montara, CA (US); John J. Flynn, West Milford, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1656 days.

This patent is subject to a terminal disclaimer.

(21) Appl. No.: 11/304,202

(22) Filed: Dec. 14, 2005

(65) Prior Publication Data

US 2006/0276897 A1    Dec. 7, 2006

Related U.S. Application Data

(63) Continuation-in-part of application No. PCT/US2005/044979, filed on Dec. 13, 2005, which is a continuation-in-part of application No. 11/053,399, filed on Feb. 8, 2005, now Pat. No. 7,591,851, and a continuation-in-part of application No. 11/053,624, filed on Feb. 8, 2005, now Pat. No. 7,601,170, and a continuation-in-part of application No. 11/053,735, filed on Feb. 8, 2005, now Pat. No. 7,776,090, and a continuation-in-part of application No. 11/053,346, filed on Feb. 8, 2005, now abandoned, and a continuation-in-part of application No. 11/093,557, filed on Mar. 30, 2005, now Pat. No. 7,763,050, and a continuation-in-part of application No. 11/093,689, filed on Mar. 30, 2005.

(60) Provisional application No. 60/635,453, filed on Dec. 13, 2004, provisional application No. 60/668,053, filed on Apr. 4, 2005, provisional application No. 60/679,377, filed on May 10, 2005, provisional application No. 60/679,361, filed on May 10, 2005, provisional application No. 60/679,363, filed on May 10, 2005, provisional application No. 60/687,765, filed on Jun. 6, 2005, provisional application No. 60/717,369, filed on Sep. 15, 2005.

(51) Int. Cl.
*A61F 2/44* (2006.01)
*A61B 17/88* (2006.01)

(52) U.S. Cl. ................................ 606/281; 623/17.11

(58) Field of Classification Search ..... 623/17.11–17.16
See application file for complete search history.

(56) References Cited

U.S. PATENT DOCUMENTS 3,867,728 A    2/1975 Stubstad et al. .................... 3/1

(Continued)

FOREIGN PATENT DOCUMENTS

DE    9304368 U    6/1993

(Continued)

OTHER PUBLICATIONS

Kirkaldy-Willis, W.H., et al., "Pathology and Pathogenesis of Lumbar Spondylosis and Stenosis," Spine, vol. 3, No. 4, Dec. 1978, pp. 319-328.

(Continued)

*Primary Examiner* — Anu Ramana

(57) ABSTRACT

Systems and method in accordance with the embodiments of the present invention can include an implant for positioning at a vertebra for resisting the expulsion of a bone graft from within an intervertebral space. The implant includes a buttress plate having an intervertebral plate and an anchoring plate connected such that the intervertebral plate can move relative to the anchoring plate.

15 Claims, 20 Drawing Sheets

U.S. PATENT DOCUMENTS

| | | | |
|---|---|---|---|
| 3,875,595 A | 4/1975 | Froning | 3/1 |
| 3,879,767 A | 4/1975 | Stubstad | 3/1 |
| 4,001,896 A | 1/1977 | Arkangel | 3/1.91 |
| 4,085,466 A | 4/1978 | Goodfellow et al. | 3/1.91 |
| 4,156,296 A | 5/1979 | Johnson et al. | 623/21.19 |
| 4,231,121 A | 11/1980 | Lewis | 623/21.16 |
| 4,349,921 A | 9/1982 | Kuntz | 3/1 |
| 4,502,161 A | 3/1985 | Wall | 3/1.91 |
| 4,714,469 A | 12/1987 | Kenna | 623/17 |
| 4,759,769 A | 7/1988 | Hedman et al. | 623/17 |
| 4,772,287 A | 9/1988 | Ray et al. | 623/17 |
| 4,863,477 A | 9/1989 | Monson | 623/17 |
| 4,904,260 A | 2/1990 | Ray et al. | 623/17 |
| 4,911,718 A | 3/1990 | Lee et al. | 623/17 |
| 5,015,255 A | 5/1991 | Kuslich | 623/17 |
| 5,047,055 A | 9/1991 | Bao et al. | 623/17 |
| 5,062,845 A | 11/1991 | Kuslich | 606/80 |
| 5,071,437 A | 12/1991 | Steffee | 623/17 |
| 5,092,866 A | 3/1992 | Breard et al. | 606/61 |
| 5,127,912 A | 7/1992 | Ray et al. | 606/61 |
| 5,147,361 A * | 9/1992 | Ojima et al. | 606/70 |
| 5,147,404 A | 9/1992 | Downey | 623/17 |
| 5,171,280 A | 12/1992 | Baumgartner | 623/17 |
| 5,192,326 A | 3/1993 | Bao et al. | 623/17 |
| 5,258,031 A | 11/1993 | Salib et al. | 623/17.15 |
| 5,300,073 A | 4/1994 | Ray et al. | 606/61 |
| 5,306,275 A | 4/1994 | Bryan | 606/61 |
| 5,306,308 A | 4/1994 | Gross et al. | 623/17 |
| 5,306,309 A | 4/1994 | Wagner et al. | 623/17 |
| 5,360,431 A | 11/1994 | Puno et al. | 606/72 |
| 5,370,697 A | 12/1994 | Baumgartner | 623/17 |
| 5,401,269 A | 3/1995 | Buttner-Janz et al. | 623/17 |
| 5,415,661 A | 5/1995 | Holmes | 606/69 |
| 5,425,773 A | 6/1995 | Boyd et al. | 623/17.15 |
| 5,437,672 A | 8/1995 | Alleyne | 606/61 |
| 5,445,639 A | 8/1995 | Kuslich et al. | 606/80 |
| 5,458,642 A | 10/1995 | Beer et al. | 623/17 |
| 5,458,643 A | 10/1995 | Oka et al. | 623/18 |
| 5,491,882 A | 2/1996 | Walston et al. | 29/419.1 |
| 5,507,823 A | 4/1996 | Walston et al. | 623/17 |
| 5,514,180 A | 5/1996 | Heggeness et al. | 623/17 |
| 5,527,312 A | 6/1996 | Ray | 606/61 |
| 5,527,314 A | 6/1996 | Brumfield et al. | 606/61 |
| 5,534,028 A | 7/1996 | Bao et al. | 623/17 |
| 5,534,030 A | 7/1996 | Navarro et al. | 623/17 |
| 5,545,229 A | 8/1996 | Parsons et al. | 623/17 |
| 5,556,431 A | 9/1996 | Buttner-Janz | 623/17 |
| 5,562,738 A | 10/1996 | Boyd et al. | 623/17.15 |
| 5,571,189 A | 11/1996 | Kuslich | 623/17 |
| 5,571,191 A | 11/1996 | Fitz | 623/17 |
| 5,577,995 A | 11/1996 | Walker et al. | 601/120 |
| 5,591,165 A | 1/1997 | Jackson | 606/61 |
| 5,603,713 A | 2/1997 | Aust et al. | 606/61 |
| 5,645,597 A | 7/1997 | Krapiva | 623/17 |
| 5,645,599 A | 7/1997 | Samani | 623/17 |
| 5,653,762 A | 8/1997 | Pisharodi | 623/17 |
| 5,674,295 A | 10/1997 | Ray et al. | 623/17 |
| 5,674,296 A | 10/1997 | Bryan et al. | 623/17 |
| 5,676,701 A | 10/1997 | Yuan et al. | 623/17 |
| 5,683,464 A | 11/1997 | Wagner et al. | 623/17 |
| 5,702,450 A | 12/1997 | Bisserie | 623/17 |
| 5,716,415 A | 2/1998 | Steffee | 623/17 |
| 5,741,261 A | 4/1998 | Moskovitz et al. | 606/61 |
| 5,766,251 A | 6/1998 | Koshino | 623/16 |
| 5,766,253 A | 6/1998 | Brosnahan, III | 623/17.16 |
| 5,824,093 A | 10/1998 | Ray et al. | 623/17 |
| 5,824,094 A | 10/1998 | Serhan et al. | 623/17 |
| 5,836,948 A | 11/1998 | Zucherman et al. | 606/61 |
| 5,860,977 A | 1/1999 | Zucherman et al. | 606/61 |
| 5,865,846 A | 2/1999 | Bryan et al. | 623/17 |
| 5,868,745 A | 2/1999 | Alleyne | 606/61 |
| 5,876,404 A | 3/1999 | Zucherman et al. | 606/61 |
| 5,879,396 A | 3/1999 | Walston et al. | 623/23.41 |
| 5,893,889 A | 4/1999 | Harrington | 623/17 |
| RE36,221 E | 6/1999 | Breard et al. | 606/61 |
| 5,951,555 A | 9/1999 | Rehak et al. | 606/61 |
| 6,001,130 A | 12/1999 | Bryan et al. | 623/17 |
| 6,014,588 A | 1/2000 | Fitz | 607/46 |
| 6,019,792 A | 2/2000 | Cauthen | 623/17 |
| 6,039,763 A | 3/2000 | Shelokov | 623/17 |
| 6,048,342 A | 4/2000 | Zucherman et al. | 606/61 |
| 6,063,121 A | 5/2000 | Xavier et al. | 623/17 |
| 6,066,325 A | 5/2000 | Wallace et al. | 424/400 |
| 6,068,630 A | 5/2000 | Zucherman et al. | 606/61 |
| RE36,758 E | 6/2000 | Fitz | 623/17 |
| 6,080,157 A | 6/2000 | Cathro et al. | 606/61 |
| 6,099,531 A | 8/2000 | Bonutti | 606/87 |
| 6,113,637 A | 9/2000 | Gill et al. | 623/17 |
| 6,132,464 A | 10/2000 | Martin | 623/17 |
| 6,132,465 A | 10/2000 | Ray et al. | 623/17.16 |
| 6,200,322 B1 | 3/2001 | Branch et al. | 606/96 |
| 6,293,949 B1 | 9/2001 | Justis et al. | 606/61 |
| 6,419,703 B1 | 7/2002 | Fallin et al. | 623/17.11 |
| 6,436,101 B1 | 8/2002 | Hamada | 606/85 |
| 6,470,207 B1 | 10/2002 | Simon et al. | 600/426 |
| 6,565,605 B2 | 5/2003 | Goble et al. | 623/17.11 |
| 6,579,318 B2 | 6/2003 | Varga et al. | 623/17.11 |
| 6,579,319 B2 | 6/2003 | Goble et al. | 623/17.11 |
| 6,610,091 B1 | 8/2003 | Reiley | 623/17.11 |
| 6,669,729 B2 | 12/2003 | Chin | 623/17.11 |
| 6,761,720 B1 | 7/2004 | Senegas | 606/61 |
| 6,764,489 B2 * | 7/2004 | Ferree | 606/279 |
| 6,764,491 B2 | 7/2004 | Frey et al. | 606/85 |
| 6,783,527 B2 | 8/2004 | Drewry et al. | 606/61 |
| 6,811,567 B2 | 11/2004 | Reiley | 623/17.11 |
| 6,843,790 B2 * | 1/2005 | Ferree | 606/279 |
| 6,902,566 B2 | 6/2005 | Zucherman et al. | 606/61 |
| 6,974,478 B2 | 12/2005 | Reiley et al. | 623/17.11 |
| 7,008,427 B2 * | 3/2006 | Sevrain | 606/71 |
| 7,101,375 B2 | 9/2006 | Zucherman et al. | 606/61 |
| 7,628,816 B2 * | 12/2009 | Magerl et al. | 623/17.16 |
| 2001/0018614 A1 | 8/2001 | Bianchi | |
| 2002/0029039 A1 | 3/2002 | Zucherman et al. | |
| 2002/0151895 A1 | 10/2002 | Soboleski et al. | |
| 2003/0004572 A1 | 1/2003 | Goble et al. | |
| 2003/0187454 A1 | 10/2003 | Gill et al. | |
| 2004/0059429 A1 | 3/2004 | Amin et al. | |
| 2004/0116927 A1 | 6/2004 | Graf | |
| 2004/0127989 A1 | 7/2004 | Dooris et al. | |
| 2004/0143264 A1 | 7/2004 | McAfee | |
| 2004/0230201 A1 | 11/2004 | Yuan et al. | |
| 2004/0230304 A1 | 11/2004 | Yuan et al. | |
| 2005/0010291 A1 | 1/2005 | Stinson et al. | |
| 2005/0049705 A1 | 3/2005 | Hale et al. | |
| 2005/0159746 A1 | 7/2005 | Grob et al. | |

FOREIGN PATENT DOCUMENTS

| | | |
|---|---|---|
| DE | 20112123 | 10/2001 |
| DE | 10135771 A1 | 2/2003 |
| FR | 2722980 | 2/1996 |
| JP | 10179622 A2 | 7/1998 |
| WO | WO 98/48717 | 11/1998 |
| WO | WO 99/23963 A1 | 5/1999 |
| WO | WO 00/38582 A1 | 7/2000 |
| WO | WO 00/53126 | 9/2000 |
| WO | WO 01/30248 A1 | 5/2001 |
| WO | WO 03/101350 A1 | 12/2003 |
| WO | WO 2004/071358 A1 | 8/2004 |

OTHER PUBLICATIONS

Kotani, Y., et al., "The effects of spinal fixation and destabilization on the biomechanical and histologic properties of spinal ligaments: An in vivo study," Spine, vol. 23, No. 6, Mar. 15, 1998, pp. 672-682.

Lemaire, J.P., et al., "Intervertebral disc prosthesis: results and prospects for the year 2000," Clinical Orthopaedics and Related Research, No. 337, 1997, pp. 64-76.

Lombardi, J.S., et al., "Treatment of Degenerative Spondylolisthesis," Spine, vol. 10, No. 9, 1985, pp. 821-827.

McMillin, C.R. et al., "Artificial Spinal Discs with up to Five Years Follow-up," 20th Annual Meeting of the Society for Biomaterials (Abstract), Apr. 5-9, 1994, pp. 89.

Nagata, H., et al., "The effects of immobilization of long segments of the spine on the adjacent and distal facet force and lumbosacral motion," Spine, vol. 18, No. 16, 1993, pp. 2471-2479.

Posner, I., et al., "A Biomechanical Analysis of the Clinical Stability of the Lumbar and Lumbosacral Spine," Spine, vol. 7, No. 4, 1982, pp. 374-389.

Rosenberg, N.J., "Degenerative Spondylolisthesis—Predisposing Factors," The Journal of Bone and Joint Surgery, vol. 57-A, No. 4, 1975, pp. 467-474.

Szpalski, M., et al., "Spine Arthroplasty: A Historical Review," Eur Spine J., vol. 11, Suppl. 2, Aug. 13, 2002, pp. S65-S84.

Tsantrizos, A., et al., "Segmental stability and compressive strength of posterior lumbar interbody fusion implants," Spine, vol. 25, No. 15, 2000, pp. 1899-1907.

Dickson, R.A., "The etiology and pathogenesis of idiopathic scoliosis," Acta Orthopaedica Belgica, vol. 58, Suppl. 1, 1992, pp. 21-25.

Dickson, R.A., "The scientific basis of treatment of idiopathic thoracic scoliosis," Acta Orthopaedica Belgica, vol. 58, Suppl.1, 1992, pp. 107-110.

Millner, P.A., et al., "Idiopathic scoliosis: biomechanics and biology," Eur. Spine J., vol. 5, 1996, pp. 362-373.

Mohaideen, A., et al., "Not all rods are Harrington—an overview of spinal instrumentation in scoliosis treatment," Pediatr. Radiol. 30, 2000, pp. 110-118.

Smith, R.M., et al., "Experimental structural scoliosis," The Journal of Bone and Joint Surgery, vol. 69, 1987, pp. 576-581.

Chiu, J.C., et al., "Translaminar Facet Fixation: An Alternative Method for Lumbar Fusion: Report of 710 Cases," http://www.spinecenter.com/papers/facet/facet.htm, Sep. 8, 2005, 12 pages.

Van Schaik, Jan P.J., et al., "Curvature of the Lower Lumbar Facet Joints: Variations at Different Levels and Relationship with Orientation," Journal of Spinal Disorders, vol. 12, No. 4, 1999, pp. 341-347.

Lu, J., et al.,"Translaminar Facet Screw Placement: an Anatomic Study," The American Journal of Orthopedics, Aug. 1998, pp. 550-555.

Ebraheim, N.A., et al.,"The Quantitative Anatomy of the Thoracic Facet and the Posterior Projection of Its Inferior Facet," Spine, vol. 22, No. 16, 1997, pp. 1811-1818.

Panjabi, M.M., et al.,"Articular Facets of the Human Spine, Quantitative Three-Dimensional Anatomy," Spine, vol. 18, No. 10, 1993, pp. 1298-1310.

Boden, S.D., et al., "Orientation of the Lumbar Facet Joints: Association with Degenerative Disc Disease," The Journal of Bone and Joint Surgery, vol. 78-A, No. 3, Mar. 1996, pp. 403-411.

Cavanaugh, J.M., et al., "Lumbar Facet Pain: Biomechanics Neuroanatomy and Neurophysiology," Survey Article, J. Biomechanics, vol. 29, No. 9, 1996, pp. 1117-1129.

Yoganandan, N., et al.,"Anatomic Study of the Morphology of Human Cervical Facet Joint," Spine, vol. 28, No. 20, 2003, pp. 2317-2323.

Dudley, et al.,"Spinal Injuries," Rod & Smith's Operative Surgery—Orthopaedics Part 1, London: Butterworth-Heinemann, 1991, pp. 637-641.

* cited by examiner

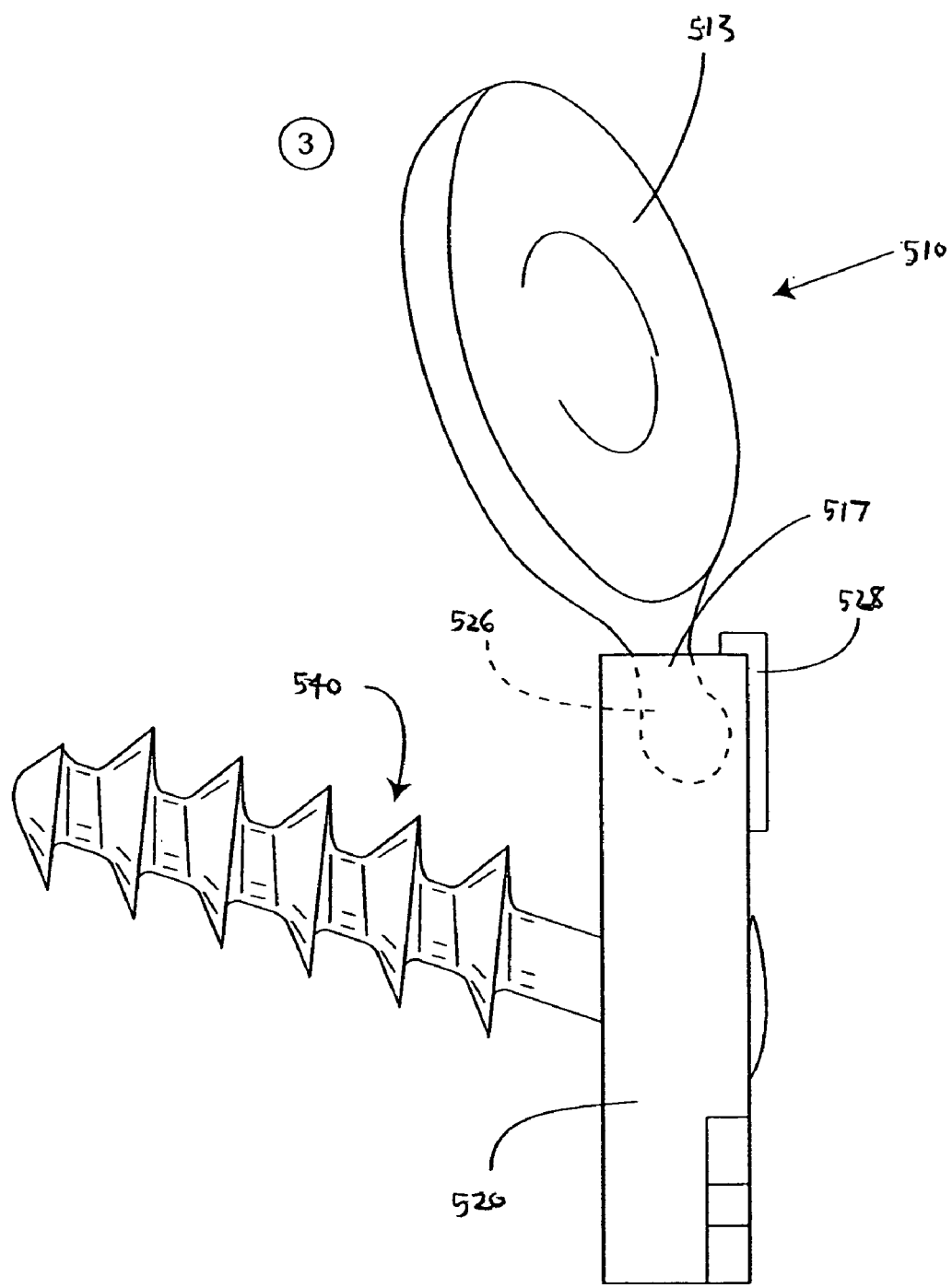
*FIG.* 11B

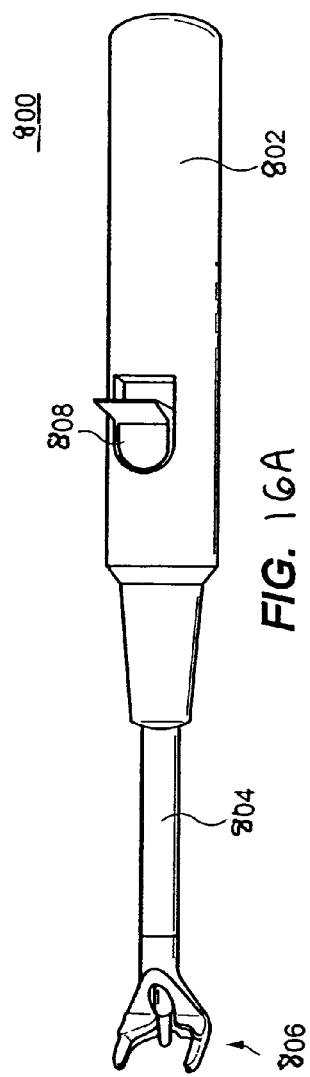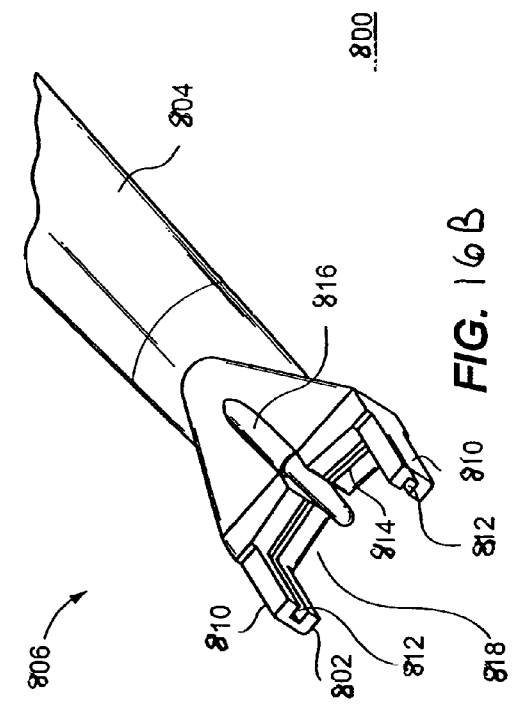
FIG. 16A
FIG. 16B

IMPLANT FOR STABILIZING A BONE GRAFT DURING SPINAL FUSION

CLAIM OF PRIORITY

This application claims priority to all the applications listed below. This application is a Continuation in part of Patent Cooperation Treaty Application, entitled INTER-FACET IMPLANT filed Dec. 13, 2005. Serial No. PCT/US2005/044979, which claims priority to United States Provisional Application, entitled, INTER-CERVICAL FACET IMPLANT AND METHOD filed Dec. 13, 2004, Ser. No. 60/635,453, and United States Provisional Application entitled INTER-CERVICAL FACET IMPLANT DISTRACTION TOOL filed Apr. 4, 2005, Ser. No. 60/668,053, and United States Provisional Application entitled INTER-CERVICAL FACET IMPLANT WITH IMPLANTATION TOOL filed May 10, 2005, Ser. No. 60/679,377, and United States Provisional Application entitled INTER-CERVICAL FACET IMPLANT WITH IMPLANTATION TOOL filed May 10, 2005, Ser. No. 60/679,361, and United States Provisional Application entitled INTER-CERVICAL FACET IMPLANT WITH IMPLANTATION TOOL filed May 10, 2005, Ser. No. 60/679,363, and United States Provisional Application entitled INTER-CERVICAL FACET IMPLANT WITH MULTIPLE DIRECTION ARTICULATION JOINT AND METHOD FOR IMPLANTING filed Jun. 6, 2005, Ser. No. 60/687,765, and United States Provisional Application entitled INTER-CERVICAL FACET IMPLANT WITH SURFACE ENHANCEMENTS filed Sep. 15, 2005, Ser. No. 60/717,369, and claims priority to and is a Continuation-in-Part of United States Utility Patent Application entitled INTER-CERVICAL FACET IMPLANT AND METHOD filed Feb. 8, 2005, Ser. No. 11/053,399 and now issued as U.S. Pat. No. 7,591,851, and is a Continuation-in-Part of United States Utility Patent Application entitled INTER-CERVICAL FACET IMPLANT AND METHOD filed Feb. 8, 2005, Ser. No. 11/053,624 and now issued as U.S. Pat. No. 7,601,170, and is a Continuation-in-Part of United States Utility Patent Application entitled INTER-CERVICAL FACET IMPLANT AND METHOD filed Feb. 8, 2005, Ser. No. 11/053,735 and now issued as U.S. Pat. No. 7,776,090, and is a Continuation in Part of United States Utility Patent Application entitled INTER-CERVICAL FACET IMPLANT AND METHOD filed Feb. 8, 2005, Ser. No. 11/053,346 now abandoned, and is a Continuation in Part of United States Utility Patent Application entitled INTER-CERVICAL FACET IMPLANT WITH LOCKING SCREW AND METHOD filed Mar. 30, 2005, Ser, No, 11/093,557 and now issue as U.S. Pat. No. 7,763,050, and is a Continuation-in-Part of United States Utility Patent Application entitled INTER-CERVICAL FACET IMPLANT AND METHOD FOR PRESERVING THE TISSUES SURROUNDING THE FACET JOINT filed Mar. 30, 2005, Ser. No. 11/093,689, which are all incorporated herein by reference.

TECHNICAL FIELD

This invention relates to interspinous process implants.

BACKGROUND OF THE INVENTION

A common procedure for handling pain associated with degenerative spinal disc disease is the use of devices for fusing together two or more adjacent vertebral bodies. The procedure is known by a number of terms, one of which is vertebral interbody fusion. Interbody fusion can be accomplished through the use of a number of devices and methods known in the art. These include screw arrangements, solid bone implant methodologies, and fusion devices which include a cage or other mechanism which is packed with bone and/or bone growth inducing substances. All of the above are implanted between adjacent vertebral bodies in order to fuse the vertebral bodies together, alleviating associated pain. One common method for fusing to vertebral body is to substitute a bone graft for a portion of a disc disposed between the vertebral bodies. The bone graft stimulates bone growth, thereby resulting in fusion. Once risk associated with a bone graft is expulsion from a point of insertion.

BRIEF DESCRIPTION OF THE DRAWINGS

FIGS. 1A and 11B are lateral views of the implant of FIGS. 9A and 9B illustrating a general range of motion of the implant.

FIGS. 16A and 16B depict an insertion tool of an embodiment of the invention.

DETAILED DESCRIPTION

Figure 1:
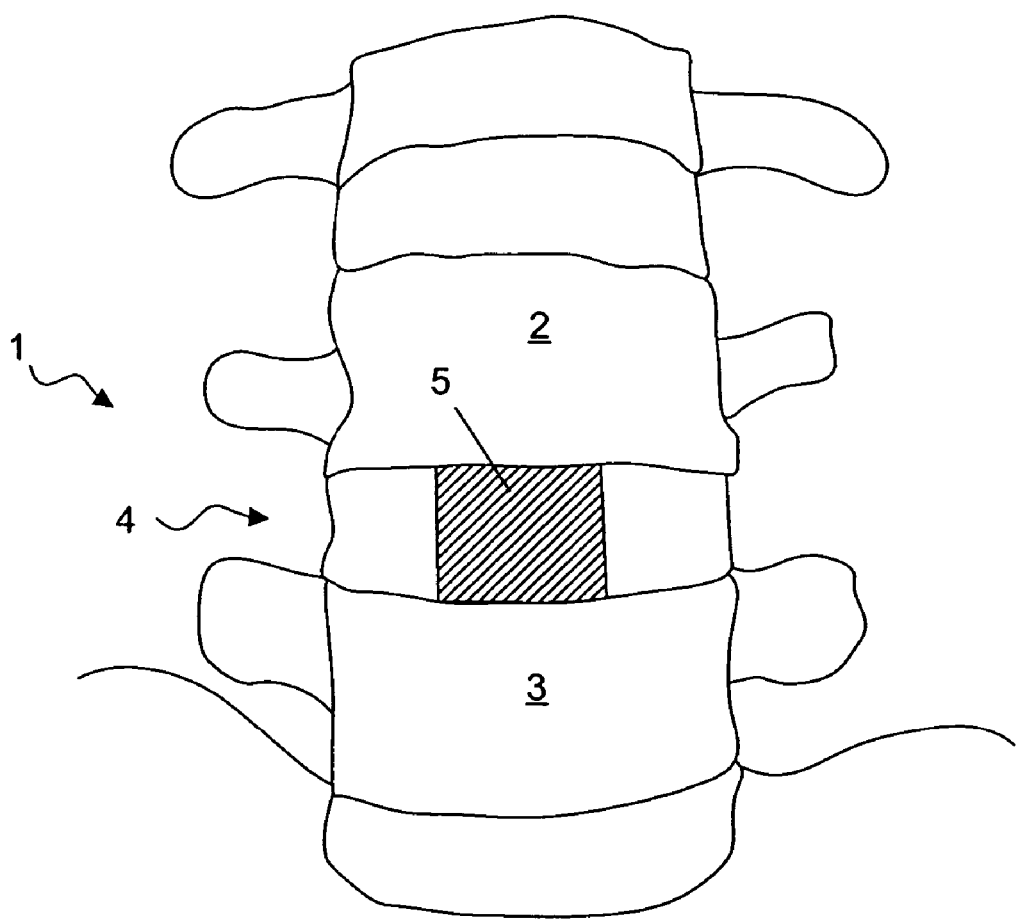
FIG. 1 is an anterior view of a targeted motion segment comprising lumbar vertebrae wherein a portion of a disc of the targeted motion segment is replaced with a bone graft.
Figure 2:
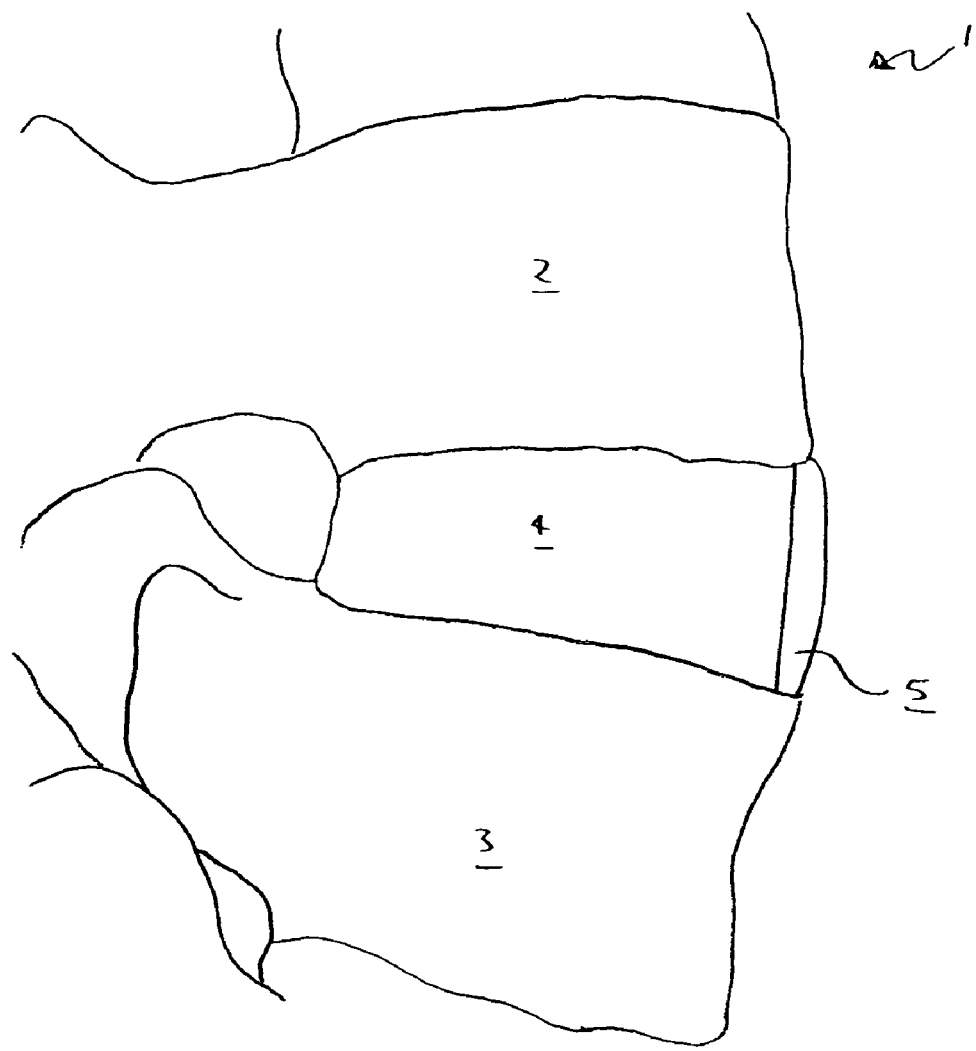
FIG. 2 is a lateral view of the targeted motion segment of FIG. 1.

FIG. 1 shows a simplified anterior view of a targeted motion segment 1 in the lumbar region of an exemplary spine. FIG. 2 shows a simplified lateral view of the targeted motion segment 1. The targeted motion segment 1 need not comprise vertebrae of the lumbar region, but rather can comprise vertebrae of any motion segment along the spine, including vertebrae of the thoracic and cervical regions. As shown, an unhealthy (i.e., defective) disc 4 is disposed between lumbar vertebrae 2,3. An unhealthy disc can result from a number of different causes such as degenerative disc disease, isthmic, degenerative or postlaminectomy spondylolisthesis, instability caused by infection or tumors, fractures, scoliosis, deformity, or some other abnormality. For patients with such conditions, abnormal and/or excessive motion at the motion segment may result in pain (e.g., from collapse of the foraminal space or herniation of the disc).

One solution for alleviating pain associated with an unhealthy disc can include stabilizing the motion segment by restricting relative movement of the respective vertebrae. Movement can be restricted by fusing together the vertebrae between which the non-healthy disc is disposed. Fusion can be achieved using a number of different devices and techniques. Spinal fusion surgery is designed to stop the motion at a painful motion segment, which in turn should decrease pain generated at the motion segment. Spinal fusion surgery can involve adding bone graft to an area of the spine to provoke a biological response that causes the bone graft to grow between the two vertebrae to form substantially continuous rigid bone, thereby stopping the motion at that motion segment. There are several types of spinal fusion surgery options, including (but not limited to) anterior interbody fusion, a technique performed from the front and including removing the disc between the two vertebrae of the targeting motion segment and inserting bone into the space created between the two vertebrae and anterior/posterior spinal fusion, a technique performed from both the front and the back.

Bone graft can be taken from a patient's hip during the spinal fusion surgery, or harvested from cadaver bone. Alternatively, a synthetic bone graft substitute can be used in place of a bone graft. For example, bone morphogenic proteins are currently used for fusion procedures. The size of the bone graft can vary at the discretion of the physician. For example, the bone graft can comprise a plug of material approximately conforming with a cavity formed within the disc, the bone graft can comprise a substitute for the disc and can be sized to substantially replace the entire disc, or the bone graft can have some other shape and size. The surgical technique applied can vary and/or influence a bone graft shape and size.

The targeted motion segment 1 of FIGS. 1 and 2 includes a bone graft 5 comprising a plug positioned within a cavity formed in the unhealthy disc 4 accessed by way of an anterior approach. Providing a point of insertion of the bone graft 5 can also provide a point of expulsion. Although the present embodiment contemplates the use of a bone graft or plug, it is to be understood that fusion devices plugs made of a metal such as titanium or a polymer such as polyetheretherketone (PEEK). Such a fusion device can include a cage that can be packed with bone to facilitate the fusion of adjacent vertebrae positioned above and below the fusion device. Such fusion devices can be seen by way of example only in U.S. Pat. Nos. 4,501,269; 4,834,757; 4,878,915; 4,961,740; 5,026,373; 5,055,104; and 5,192,327 which are incorporated herein by reference. Further it is to be understood that although an anterior approach is described above, the embodiments of the invention can also be used for a posterior approach.

Figure 3A:
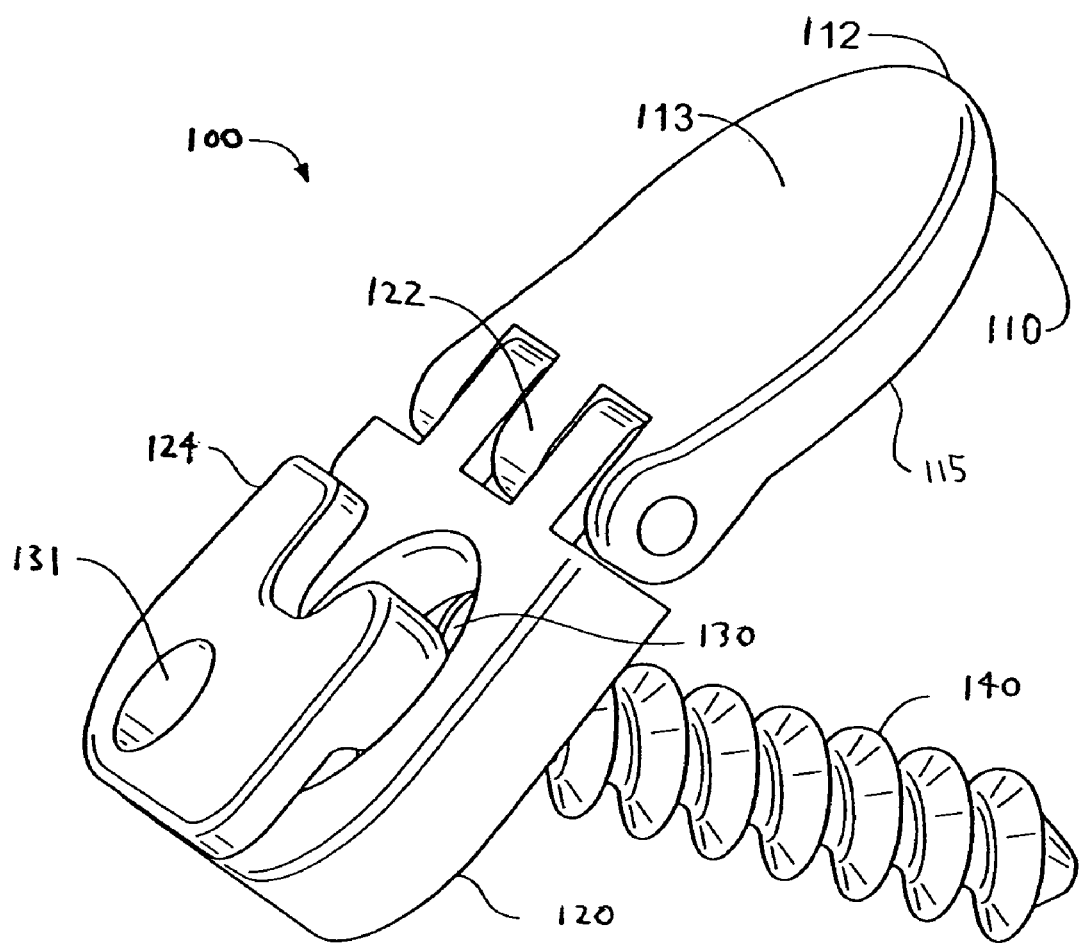
FIG. 3A is a perspective view of an embodiment of an implant in accordance with the present invention for stabilizing the bone graft of FIG. 1.
Figure 3B:
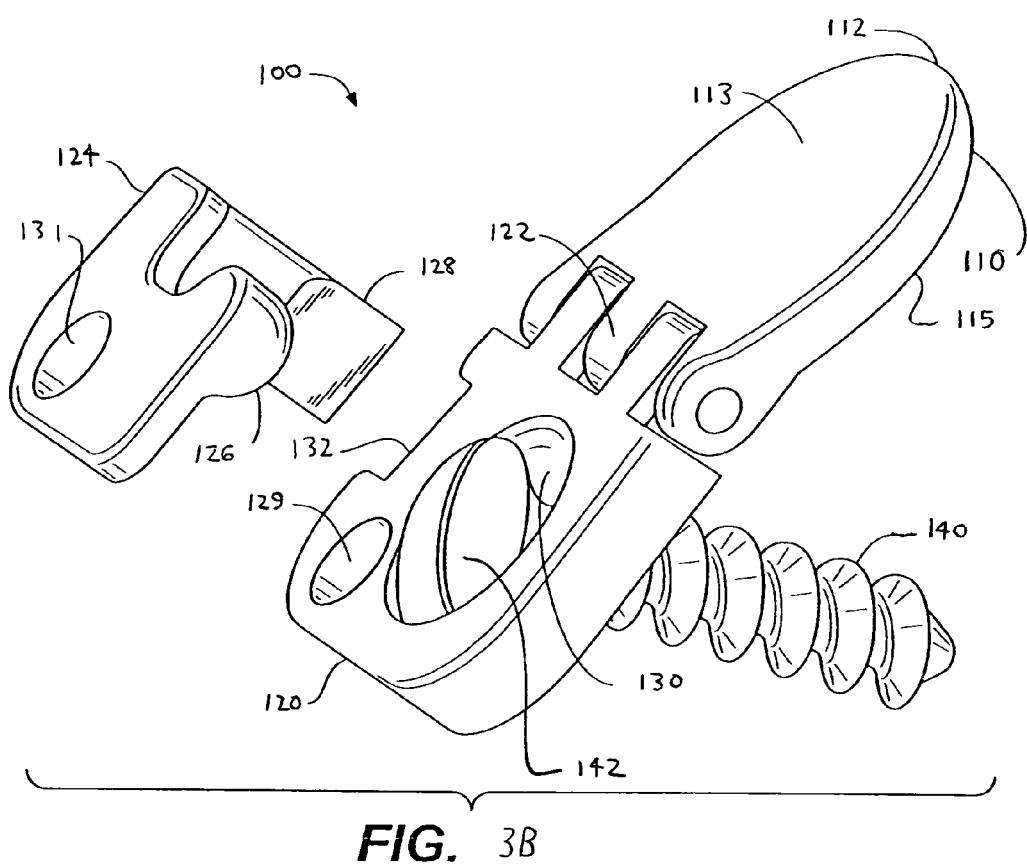
FIG. 3B is a partially exploded perspective view of the implant of FIG. 3A.
Figure 4A:
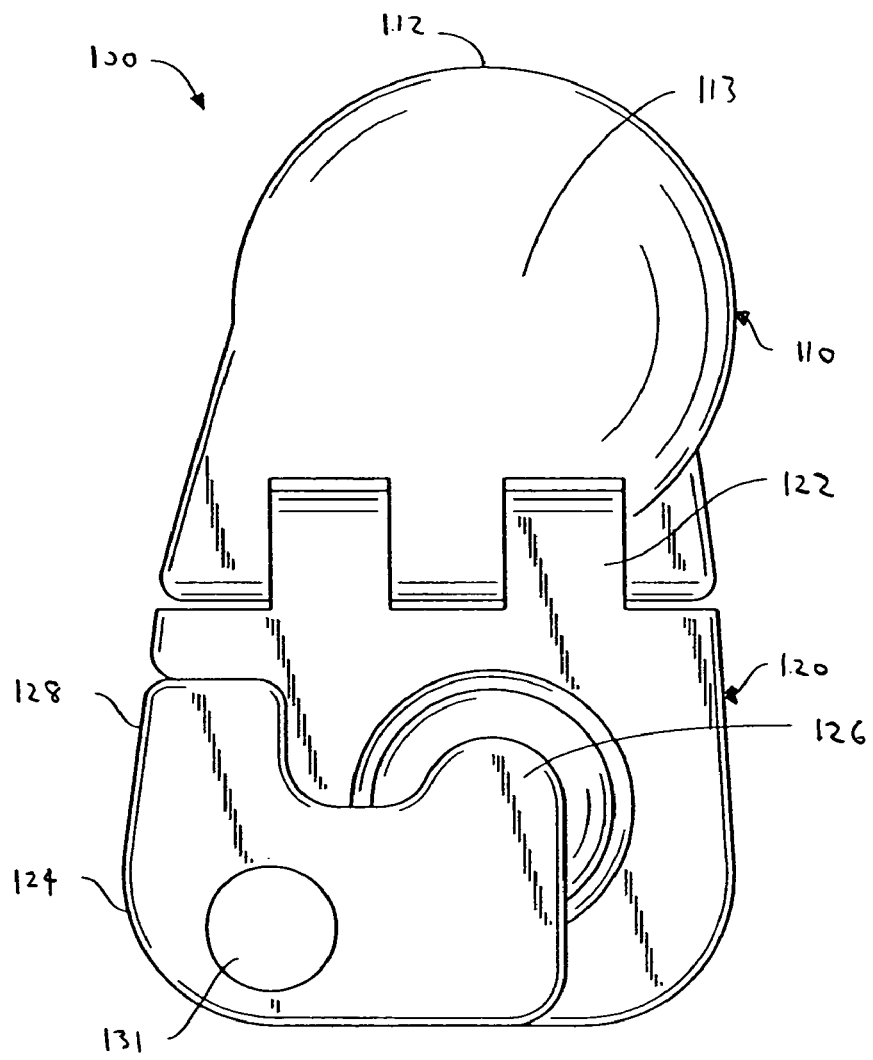
FIG. 4A is an anterior view of the implant of FIG. 3A.
Figure 4B:
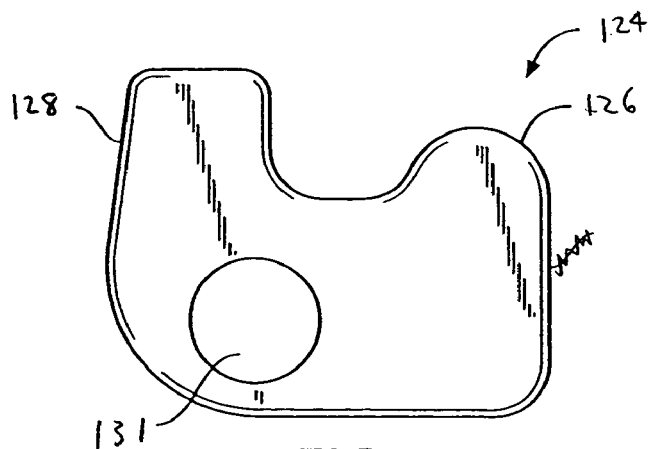
FIG. 4B is an anterior view of a locking plate of the implant of FIG. 3A.
Figure 5A:
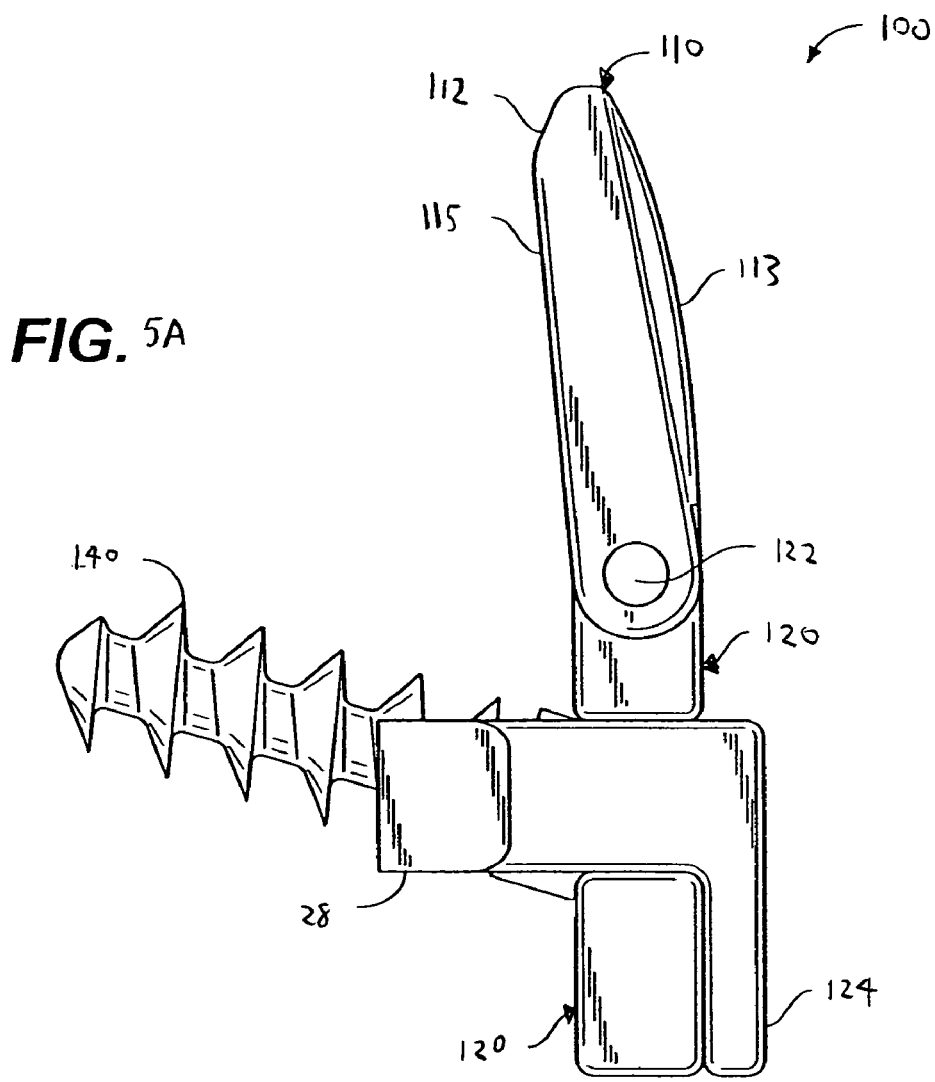
FIG. 5A is a lateral view of the implant of FIG. 3A.
Figure 5B:
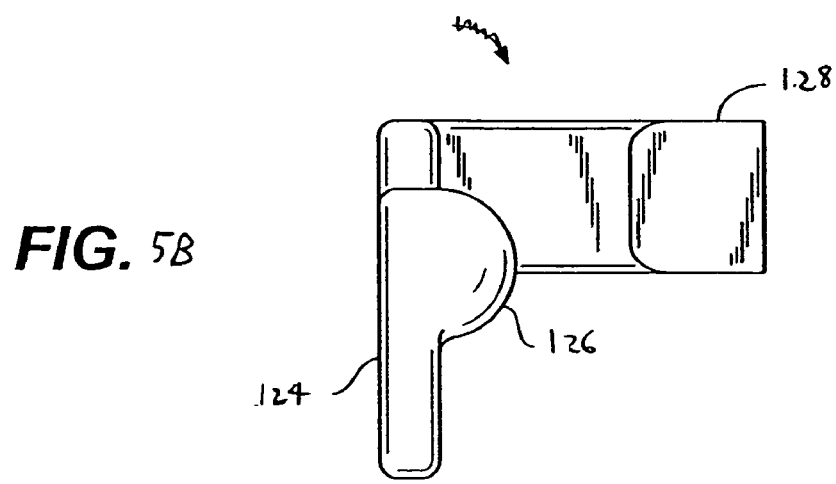
FIG. 5B is a reverse lateral view of the locking plate of FIG. 3A showing a keel and a protuberance of the locking plate.
Figure 13:
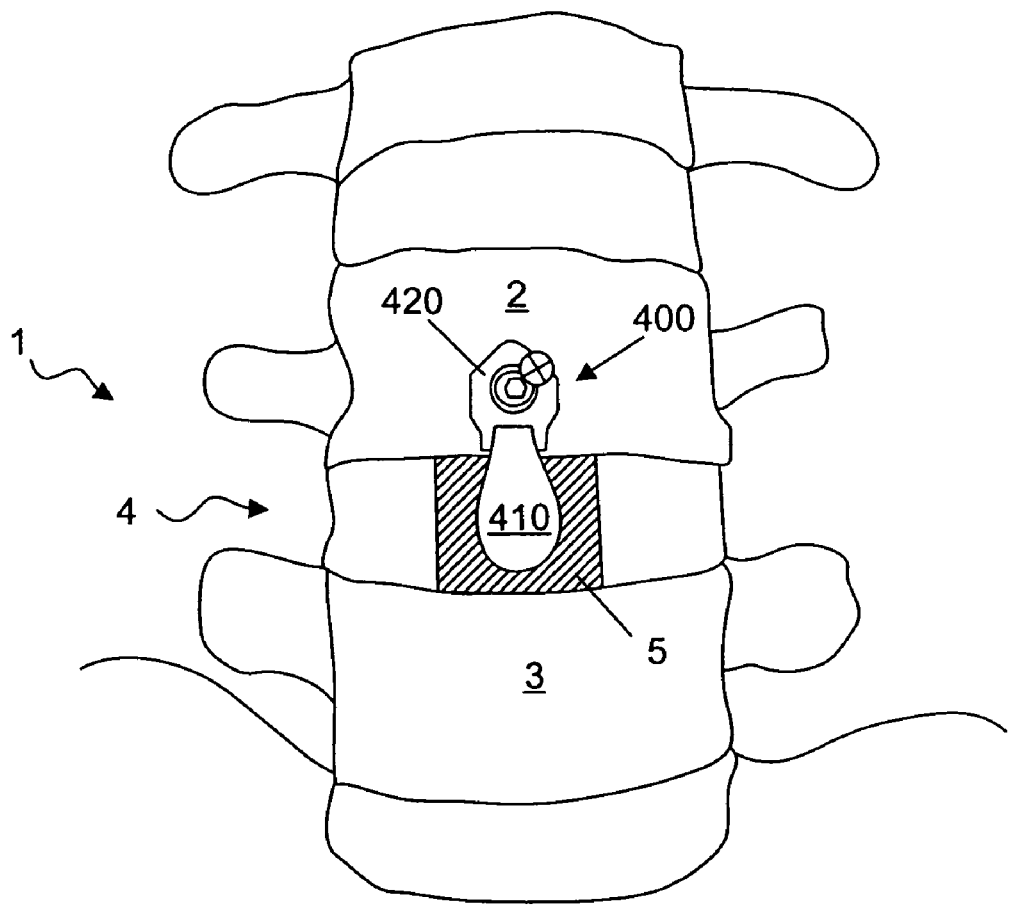
FIG. 13 is an anterior view of a targeted motion segment comprising lumbar vertebrae having a bone graft positioned in place of a portion of the disc and an implant arranged to resist expulsion of the bone graft.
Figure 14:
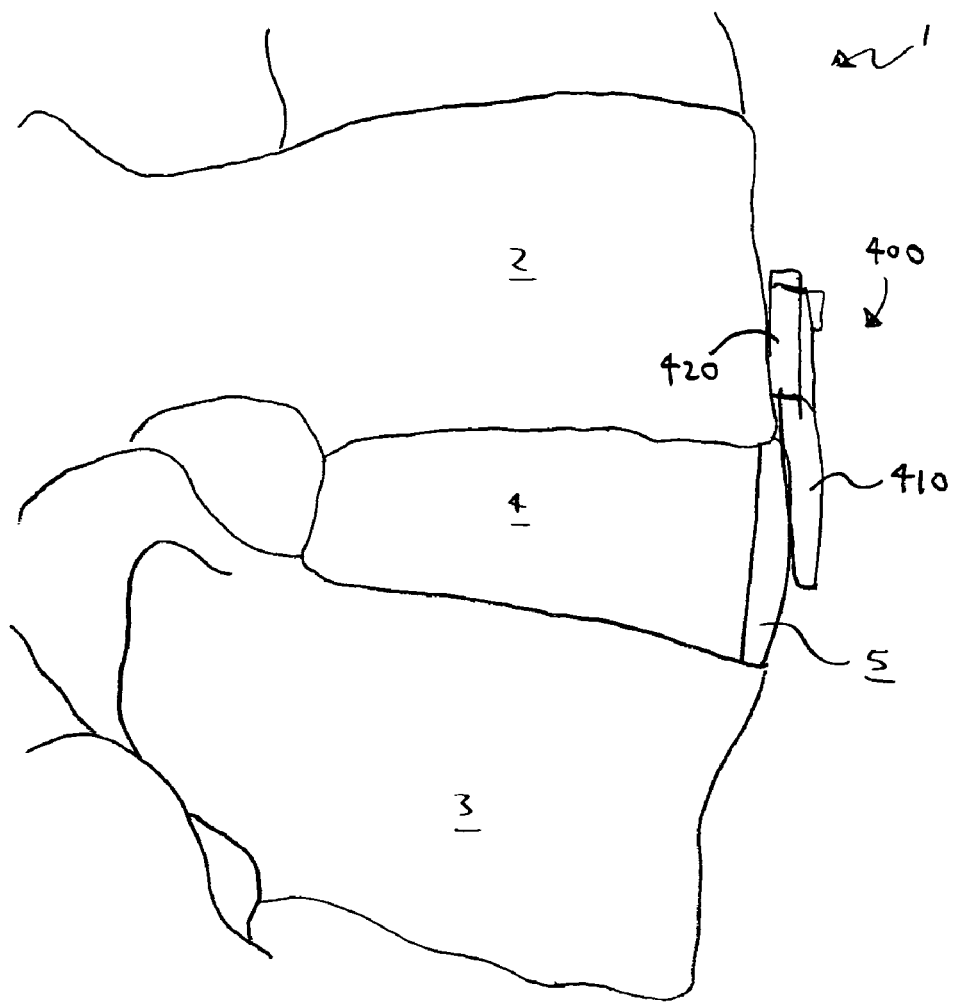
FIG. 14 is a lateral view of the targeted motion segment of FIG. 13.

An implant in accordance with the present invention can comprise a buttress plate 100 positionable such that at least a portion of the buttress plate 100 resists expulsion of a bone graft disposed within a cavity such as shown in FIGS. 1 and 2. Referring to FIG. 3A-5B, an embodiment of such an implant is shown. The implant is a buttress plate 100 having a vertebral plate (also referred to herein as an anchoring plate) 120 and an intervertebral plate 110 extending from the anchoring plate 120 and connected to the anchoring plate 120 by way of a hinge 122. The intervertebral plate 110 as shown in FIG. 3A can be saucer-shaped; however, as with all embodiments described herein, the intervertebral plate 110 alternatively have some other shape, such as square. The hinge 122 allows the anchoring plate 120 to bend at a wide range of angles relative to the intervertebral plate 110. The hinge 122 is designed so that it restricts the motion of the intervertebral plate 110 to preferably remaining about parallel with the anchoring plate 120 as seen in FIG. 3A. Such restricted motion can be accomplished by extending a flange from the anterior surface of the anchoring plate 120 so that the anterior surface 113 of the intervertebral plate 110 contacts the flange and thus restricts motion of the intervertebral plate 110 when the intervertebral plate 110 is about parallel with the anchoring plate as seen in FIG. 3A. Accordingly this restriction allows the buttress plate 100 to retain the fusion plug in place between the vertebrae as depicted in FIGS. 13 and 14. The hinge 122 however, allows the intervertebral plate 110 rotate clockwise in FIG. 3A and thus to approach the posterior surface of the anchoring plate 120. Range of motion can facilitate positioning and insertion of the intervertebral plate 110 into an incision within a patient, the anatomy of which can be highly variable among individuals. This characteristic also applies to embodiments described below, which have a hinge or which are otherwise enabled to bend by some equivalent structure or material property. The intervertebral plate 110 can be curved or rounded at a distal end 112 (FIG. 5A). The intervertebral plate 110 can include an anterior surface 115 having a shape generally conforming with a shape of the outer surface of the bone graft, although the shape need not be identical to that of the bone graft. The intervertebral plate 110 can further include an anterior surface 113 having a shape approximating that of the bone graft and/or the disc replaced by the bone graft, so that interference, friction or irritation between the buttress plate 100 and tissues and structures in close proximity to and/or associated with the unhealthy disc. The surfaces 113,115 of the intervertebral plate 110 can vary in shape and size; however, in a preferred embodiments, the surfaces 113,115 should be shaped (1) to distribute a force applied to the surface by movement of a bone graft across the surface, and (2) to minimize interference with other tissues and/or structures surrounding the intervertebral plate 110.

The anchoring plate 120, when implanted in the spine, is positioned adjacent to one of the upper and lower vertebrae associated with the targeted motion segment. As shown, the anchoring plate 120 has a generally square shape with rounded corners; however, in other embodiments (and with all embodiments herein described) the anchoring plate 120 can have any number of shapes so long as the anchoring plate 120 provides sufficient support for anchoring the implant 100 in position and so long as the anchoring plate 120 allows a desired range of motion for the intervertebral plate 110 during implantation. The anchoring plate 120 has a bore 130 therethrough, the bore 130 being adapted to receive a bone screw 140 for securing the anchoring plate 120 to the corresponding vertebra, thereby anchoring the buttress plate 100. In an embodiment, a locking plate 124 can be mated with the anchoring plate 120 to resist rotation of the anchoring plate 120. As shown, a keel 128 extends from the locking plate 124 and has a wedge shaped distal end adapted to pierce the vertebra with which the bone screw 140 is associated. The keel 128 aligns with a groove 123 through an edge of the anchoring plate 120 to guide and align the keel 128 as the keel 128 cuts into the vertebra. The locking plate 124 includes a protuberance 126 that is positioned at least partially within the bore 130 and in contact or near contact with a head 142 of the bone screw 140. The locking plate 124 further includes a bore 131 that can accept a machine screw (not shown) which passes through to an aligned bore 129 in the anchoring plate 120 to hold the locking plate 124 and the anchoring plate 120 together without rotational displacement relative to each other. The locking plate 124 thus serves at least two functions: (1) maintaining the position of the bone screw 140 with the protuberance 126 so that the bone screw 140 does not back out; and (2) using the keel 128 to prevent rotation of the buttress plate 100 relative to the vertebra with which the implant buttress plate 100 is connected. In other embodiments, other mechanisms can be employed to resist movement of the anchoring plate 120 relative to the vertebra. Implants in accordance with the present invention are not intended to be limited to those embodiments described in detail herein, but rather are meant to apply to all such embodiments comprising anchoring plates moveably connected with intervertebral plates for resisting expulsion of a bone graft.

Figure 6:
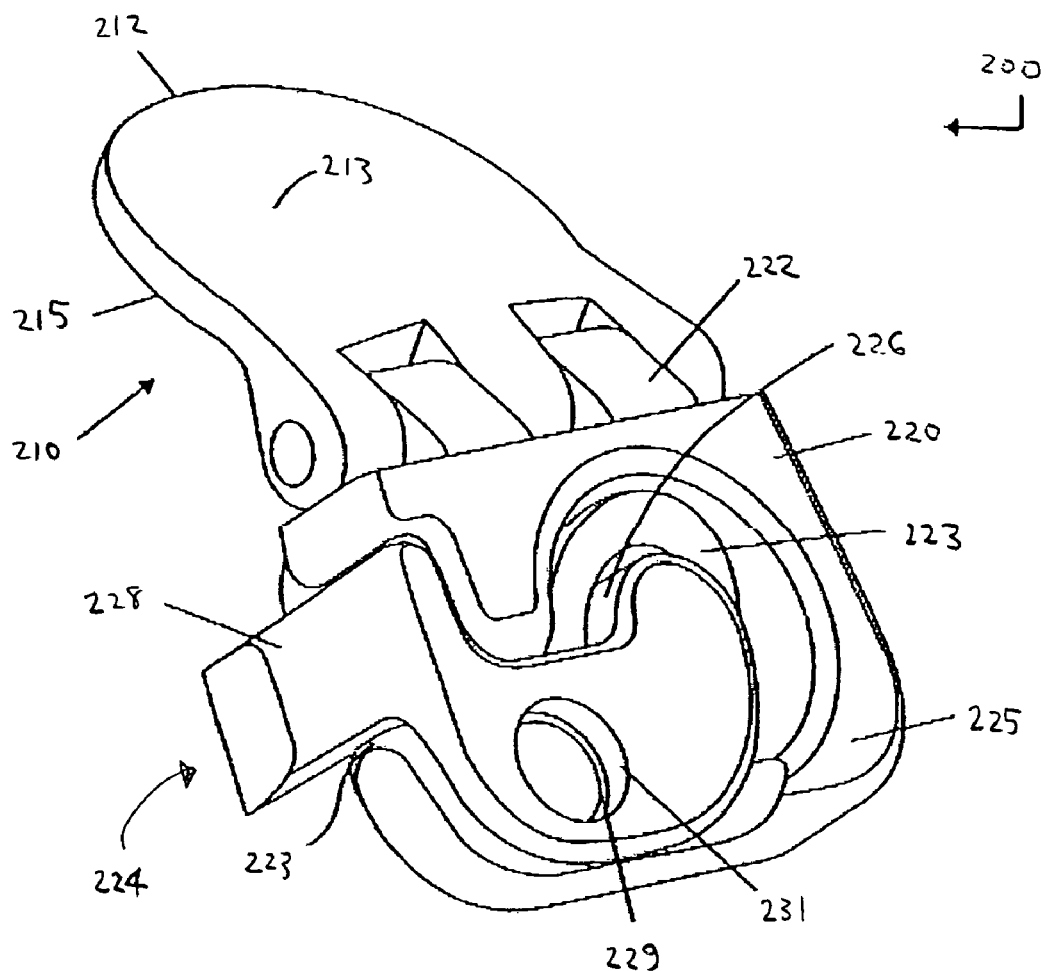
FIG. 6 is a perspective view of an alternative embodiment of an implant in accordance with the present invention having an anchoring plate with a recess for receiving a locking plate.
Figure 7B:
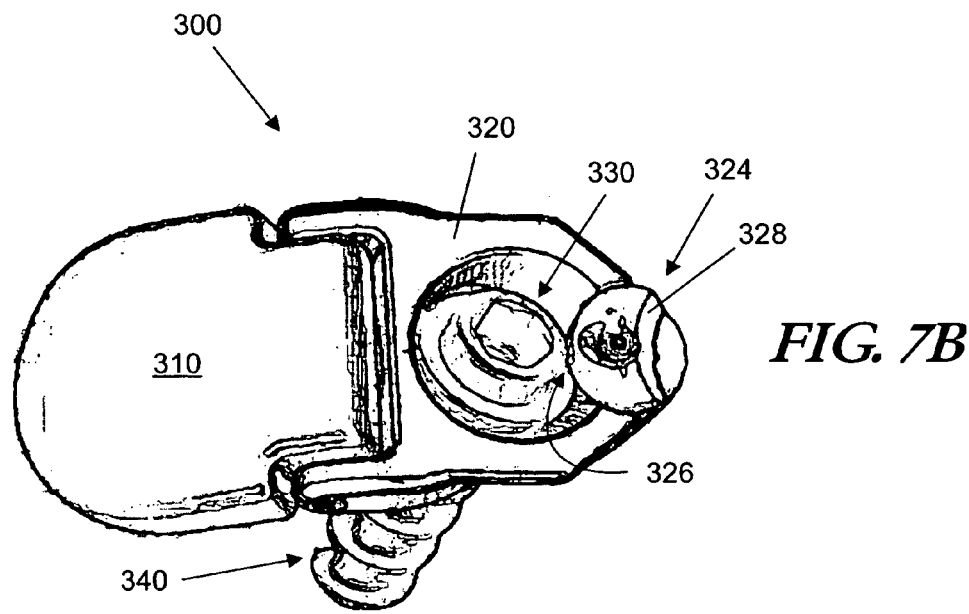
FIG. 7B is a perspective view of the implant of FIG. 7B wherein the locking cam in arranged at a second position.
Figure 7A:
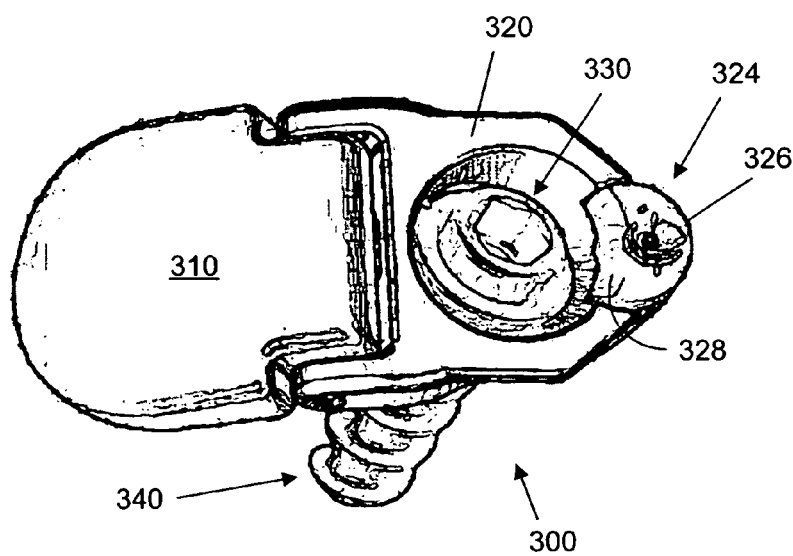
FIG. 7A is a perspective view of a still further embodiment of the implant in accordance with the present invention having a locking cam in substitution of a locking plate, the cam being arranged at a first position.

FIG. 6 illustrates an alternative embodiment of an implant in accordance with the present invention, wherein an anchoring plate 220 can include a recessed anterior surface 223 for receiving the locking plate 224 so that the locking plate 224 is flush with the exposed anterior surface 225 of the anchoring plate 220 when the protuberance 226 is urged against the bone screw 240 and the keel 228 of the locking plate 224 is inserted into the vertebra. In still other embodiments, some other structure can be employed to resist movement of the seated bone screw within the first bore. Referring to the embodiments of FIGS. 7A and 7B, a cam 324 can be rotatably associated with the anchoring plate 320 so that the first bore 330 can be selectably obstructed or unobstructed, thereby allowing a bone screw 340 to be received within the first bore 330, or resisting movement of the bone screw 340 seated within the first bore 330. As shown in FIG. 7A, the cam 324 can have a shape such that at a first position the surface 328 of the cam is approximately flush with the first bore 330, allowing a bone screw 340 to pass through the first bore 330. Rotated to a second position (FIG. 7B), a protruding portion 326 of the surface of the cam 324 can extend across at least a portion of the first bore 330, blocking the bone screw 340 seated within the first bore 330 and preventing the bone screw 340 from backing out of the first bore 330. The cam 324 can include features 331 (e.g., indentations) that can allow the cam to be grasped with a tool (not shown), and thus rotated to the desired position. As shown, the cam 324 is positioned within a slot of the anchoring plate 320 so that the cam 324 does not protrude undesirably from the surface of the anchoring plate 320.

Except as otherwise noted above, the embodiment shown in FIGS. 3A-5B is similar to embodiments shown in FIGS. 6-8B. Accordingly, the remaining elements on the 200 and 300 series of element numbers are preferably substantially similar to the described elements in the 100 series of element numbers, as set forth above. Thus, by way of example, elements 223, 228, 229 and 230 are similar, respective elements 123, 128, 129 and 130.

Figure 8A:
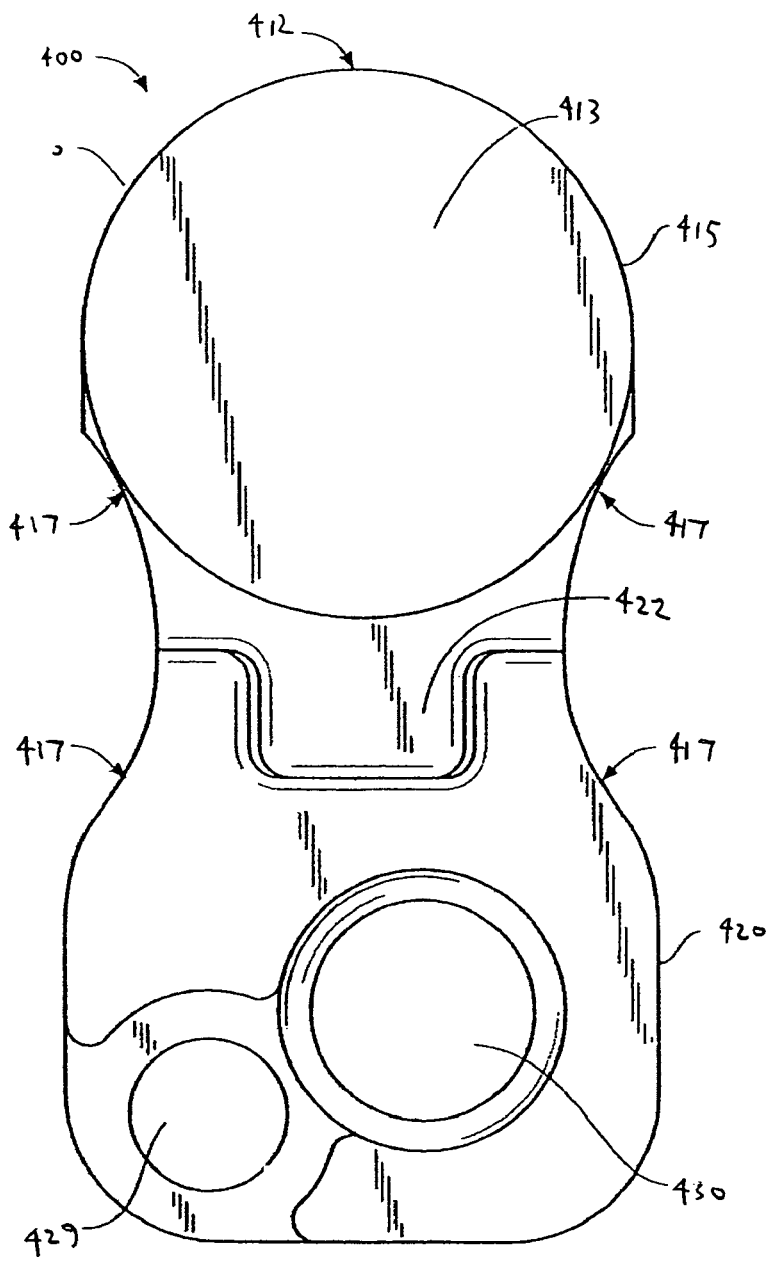
FIG. 8A is an anterior view of another embodiment of the implant in accordance with the present invention having a bore for receiving a locking screw in substitution of a locking plate.
Figure 8B:
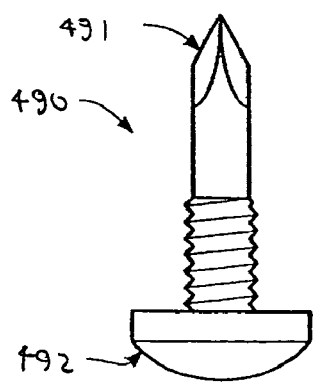
FIG. 8B is a lateral view of a locking screw for use with the implant of FIG. 8A.

FIG. 8A is an anterior view of a further embodiment of an implant in accordance with the present invention. The implant comprises a buttress plate 400 including an intervertebral plate 410 that optionally includes a tapered or thinned distal end 412. The intervertebral plate 410 is pivotably connected with an anchoring plate 420 by a hinge 422. As seen in the plan view of FIG. 8A, the implant 400 is substantially hourglass shaped. The hinge 422 is narrower than the intervertebral plate 410, with the hinge 422 sitting at substantially an isthmus 417 between intervertebral plate 410 and the anchoring plate 420. The curved edges, or fillets, about the hinge 422 distribute more evenly load-bearing stress on the intervertebral plate 410, and prevent stress concentrations about the edges.

As above, the intervertebral plate 410 preferably includes an anterior surface 415 having a shape approximately conforming with a shape of the contact surface of the bone graft and/or the outer surface of the disc. The curve can have a uniform thickness, or it can have a varied thickness. Further, the lateral edges of the intervertebral plate 410 are curved or rounded, for distribution of load-bearing stress. As with embodiments described above, the hinge 422 allows the implant 400 to pivot relative to the anchoring plate 420.

The buttress plate 400 is mechanically prevented from pivoting away from the bone graft when the anchoring plate 420 is correctly connected with a vertebra. The buttress plate 400 thus resists expulsion of a bone graft. Once the anchoring plate 420 is positioned adjacent to the vertebra, a bone screw 440, can be inserted through a bore 430 through the anchoring plate 420 and embedded into the bone of the vertebra.

The anchoring plate 420 further includes a second bore 429 which is preferably arranged medially relative to the first bore 430. The second bore 429 is adapted to accept a locking screw 490 (FIG. 8B), which preferably includes a chisel point 491. The locking screw 490 is received by the second bore 429 and the chisel point 491 self-cuts a bore into the bone. The locking screw 490 preferably is inserted through the second bore 429 and embedded into the bone, after the bone screw 440 is embedded into the bone through the first bore 430. The position of the second bore 429, i.e., medial to the first bore 430, is more centrally located relative to the corresponding vertebra so that it embeds in stronger bone tissue than if the second bore 429 were located more laterally. The locking screw 490, in combination with the bone screw 440 prevents rotational movement of the buttress plate 400 relative to the vertebra. Further, a head 492 of the locking screw 490 can overlap at least a portion of the head 442 of the bone screw 440 in the first bore 430, coming into contact or near contact to prevent the bone screw 440 from backing out of the bone of the vertebra.

Embodiments of the invention can be made without a hinge, as long as the connection between the intervertebral plate and the anchoring plate is flexible enough to allow the anchoring plate to be bent relative to the intervertebral plate in order to fit the anatomy of the patient.

Referring to FIGS. 9A through 11B, a still further embodiment of an implant in accordance with the present invention can comprise a buttress plate 500 including an intervertebral plate 510 connected with an anchoring plate 520 by a spheroidal joint arrangement 538 or otherwise shaped multiple direction articulation joint arrangement. As shown, the intervertebral plate 510 has a saucer shape, but as described in further detail below (and as described in previous embodiments above), in other embodiments the intervertebral plate 510 can have some other shape so long as a desired obstruction is achieved. The intervertebral plate 510 includes a handle-like structure necking at an isthmus 517 and terminating at a pivot end 526. In an embodiment, the pivot end 526 is substantially spherical, ovoidal, or similarly rounded in shape. As shown, the anchoring plate 520 has a generally square shape with rounded corners; however, in other embodiments the anchoring plate 520 can have any number of shapes so long as the anchoring plate 520 provides sufficient support for anchoring the implant 500 in position and so long as the anchoring plate 520 allows a desired range of motion for the intervertebral plate 510 during implantation. The anchoring plate 520 includes a cavity 527 within which the pivot end 526 is held. The spheroidal joint arrangement 538 comprises the pivot end 526 and the cavity 527 and as described below allows the intervertebral plate 510 to tilt and swivel as desired relative to the anchoring plate 520.

Figure 9A:
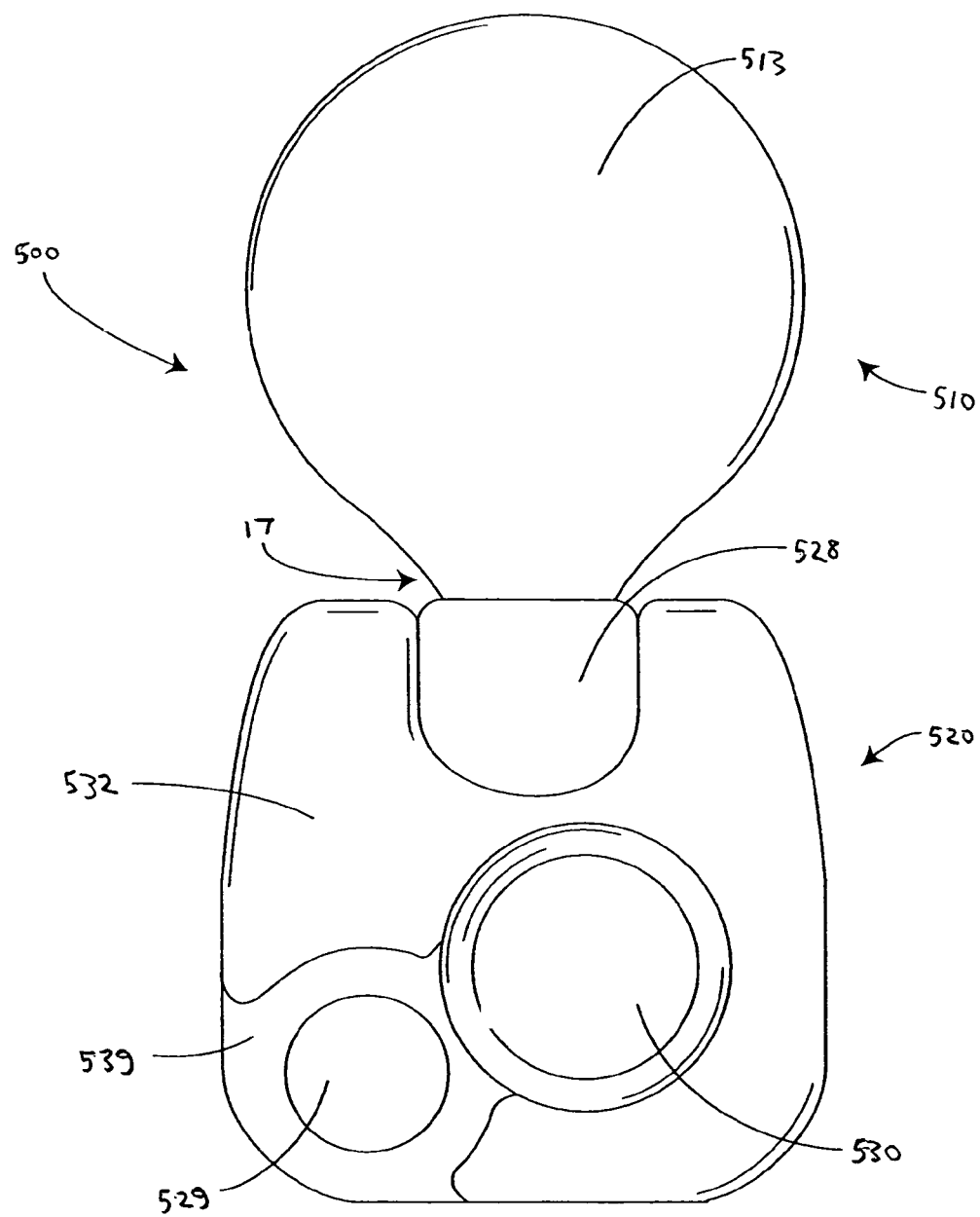
FIGS. 9A and 9B are anterior and posterior views of still another embodiment of an implant in accordance with the present invention.
Figure 9B:
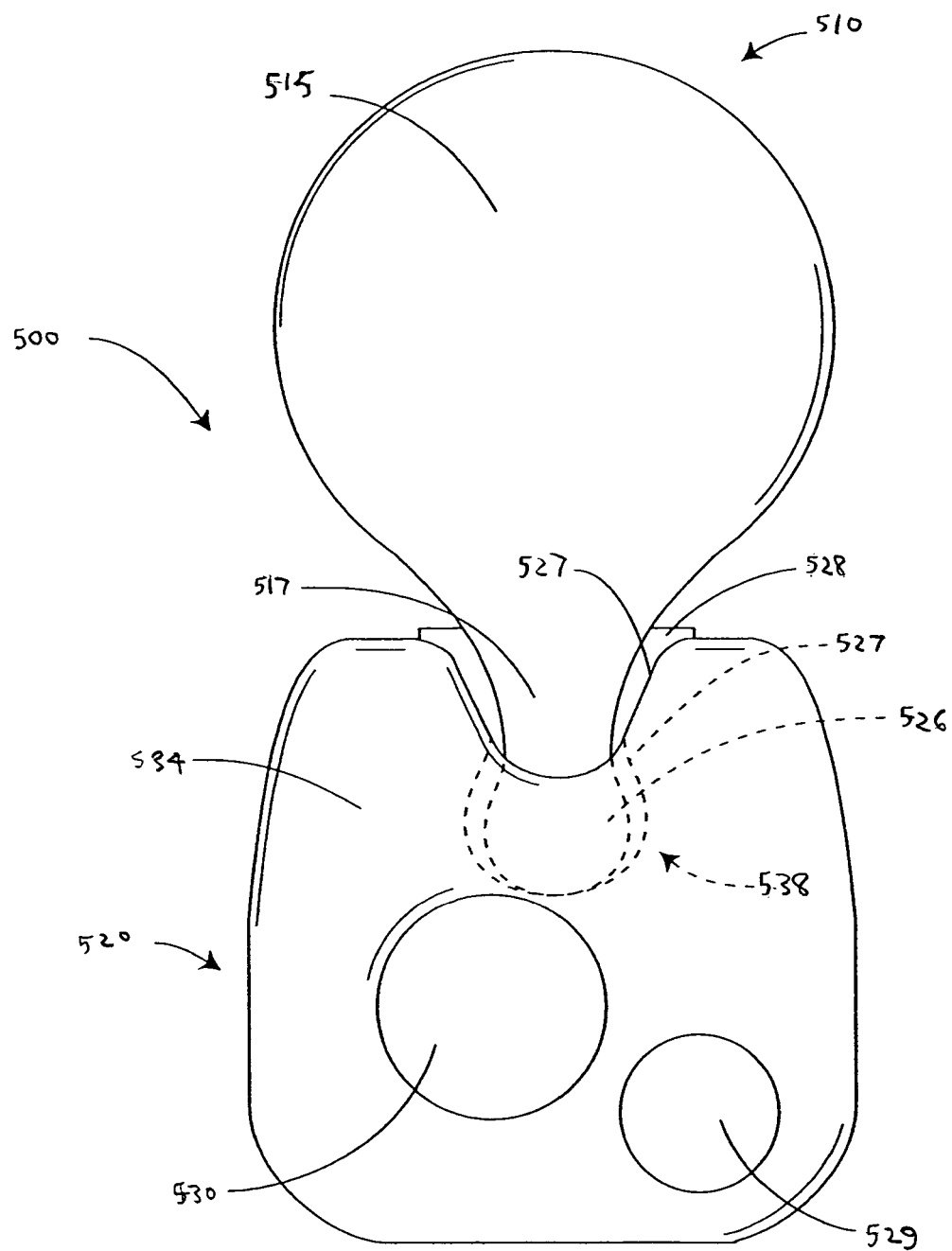
Figure 10:
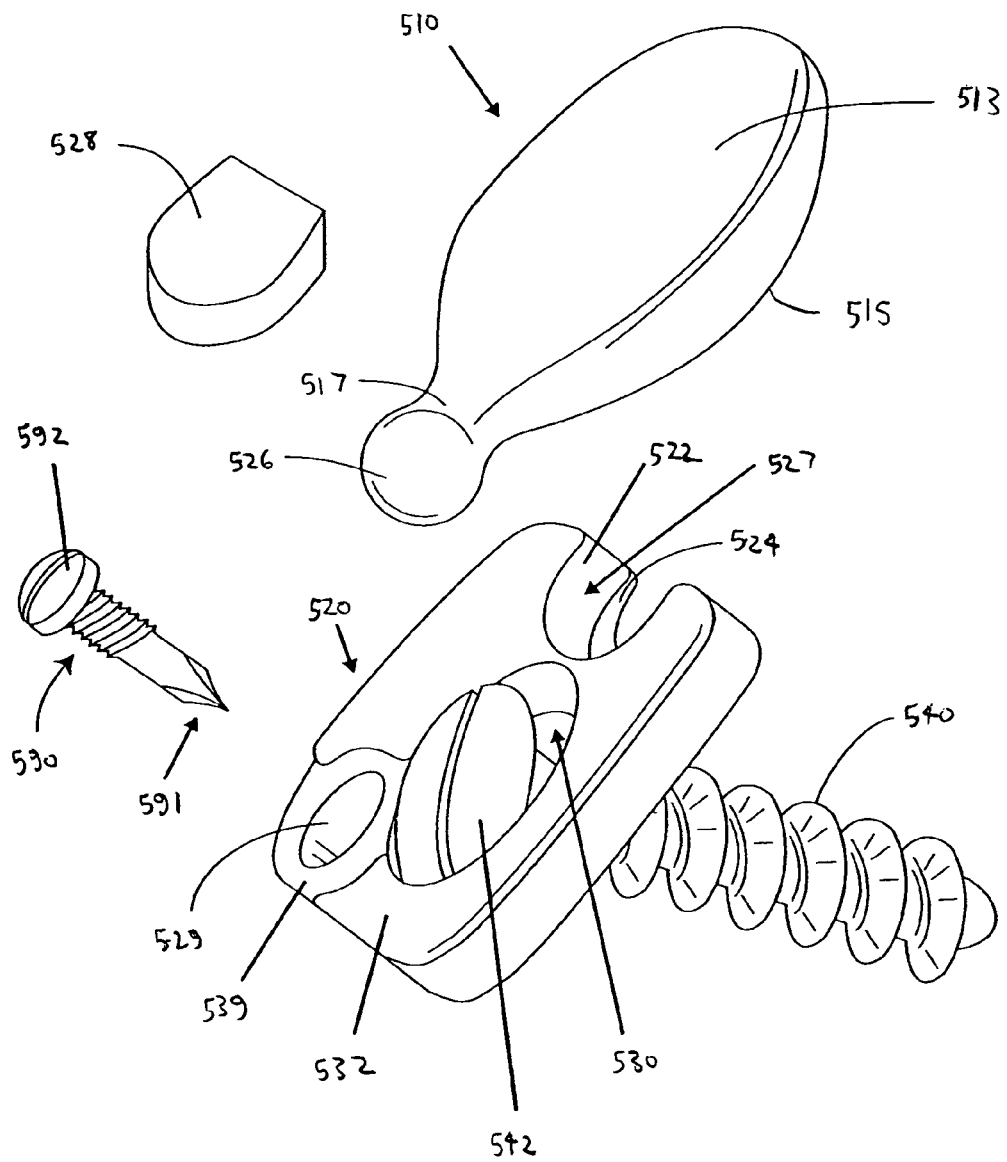
FIG. 10 is a partially exploded perspective view of the implant of FIGS. 9A and 9B.

FIG. 9A is an anterior view showing an anterior face 532 of the anchoring plate 520, while FIG. 9B is a posterior view showing a posterior face 534 of the anchoring plate 520. The anchoring plate 520 includes a posterior notch 524 (see FIG. 10) or other indentation formed along the edge of the posterior face 534 and an anterior notch 522 or other indentation formed along the anterior face 532. The posterior and anterior notches 524,522 are generally aligned with one another along the edge of the anchoring plate 520 and are associated with the cavity 527. The notches 522,524 confine movement of the intervertebral plate 510 in the anterior and posterior directions relative to the anchoring plate 520, allowing the intervertebral plate 510 to tilt at varying degrees of angle in an anterior and posterior direction. Referring to FIG. 10, the anterior notch 524 can have a wider width than the posterior notch 522 and is sized to provide the pivot end 526 of the intervertebral plate 510 with access to the cavity 527 so that the pivot end 526 can be inserted into the cavity 527. Once the pivot end 526 is positioned within the cavity 527 a plug 528 can be mated with the anchoring plate 520 to lock the pivot end 526 in place within the cavity 527 and to further limit freedom of movement of the intervertebral plate 510, particularly limiting tilting of the intervertebral plate 510 in an anterior direction that is in a direction away from a fusion plug in order to assist in retaining the fusion plug in place between vertebrae. The plug 528 can be press fit to the anterior notch 522 and further welded or otherwise fixedly fastened with the anchoring plate 520.

As can further be seen in FIGS. 9A through 10 the anchoring plate 520 has a first bore 530 therethrough. The first bore 530 can accept a bone screw 540 to secure the anchoring plate 520 preferably to one of the vertebrae, thereby anchoring the implant 500. The bone screw 540 preferably has a head 542 that can accept a tool chosen for the surgical procedure whether a wrench, screwdriver, or other tool. The anchoring plate 520 further has a second bore 529 which is preferably positioned medially, relative to the first bore 530. The second bore 529 through the anchoring plate 520 is adapted to accept a locking screw 590 having a chisel point 591. The locking screw 590 is received by the second bore 529 and the chisel point 591 self-cuts into the bone. The locking screw 590 is preferably inserted through the second bore 529 and embedded in the bone after the bone screw 540 is embedded in the bone through the first bore 530. The locking screw 590, in combination with the bone screw 540, prevents rotational displacement of the anchoring plate 520 relative to the vertebra. The second bore 529 is preferably positioned so that a head 592 of the locking screw 590 overlaps at least a portion of the head 542 of the bone screw 540. As the locking screw 590 is received by the second bore 529, the head 592 of the locking screw 590 comes in contact or near contact over the head 542 of the bone screw 540, blocking movement of the head 542 and preventing the first bone screw 540 from backing out of the bone of the vertebra and the first bore 530. The anterior face 532 of the anchoring plate 520 can optionally include a recessed portion 539 and/or the second bore 529 can be countersunk, so that the locking screw 590 does not protrude farther from the anterior face 532 than desired.

Figure 11A:
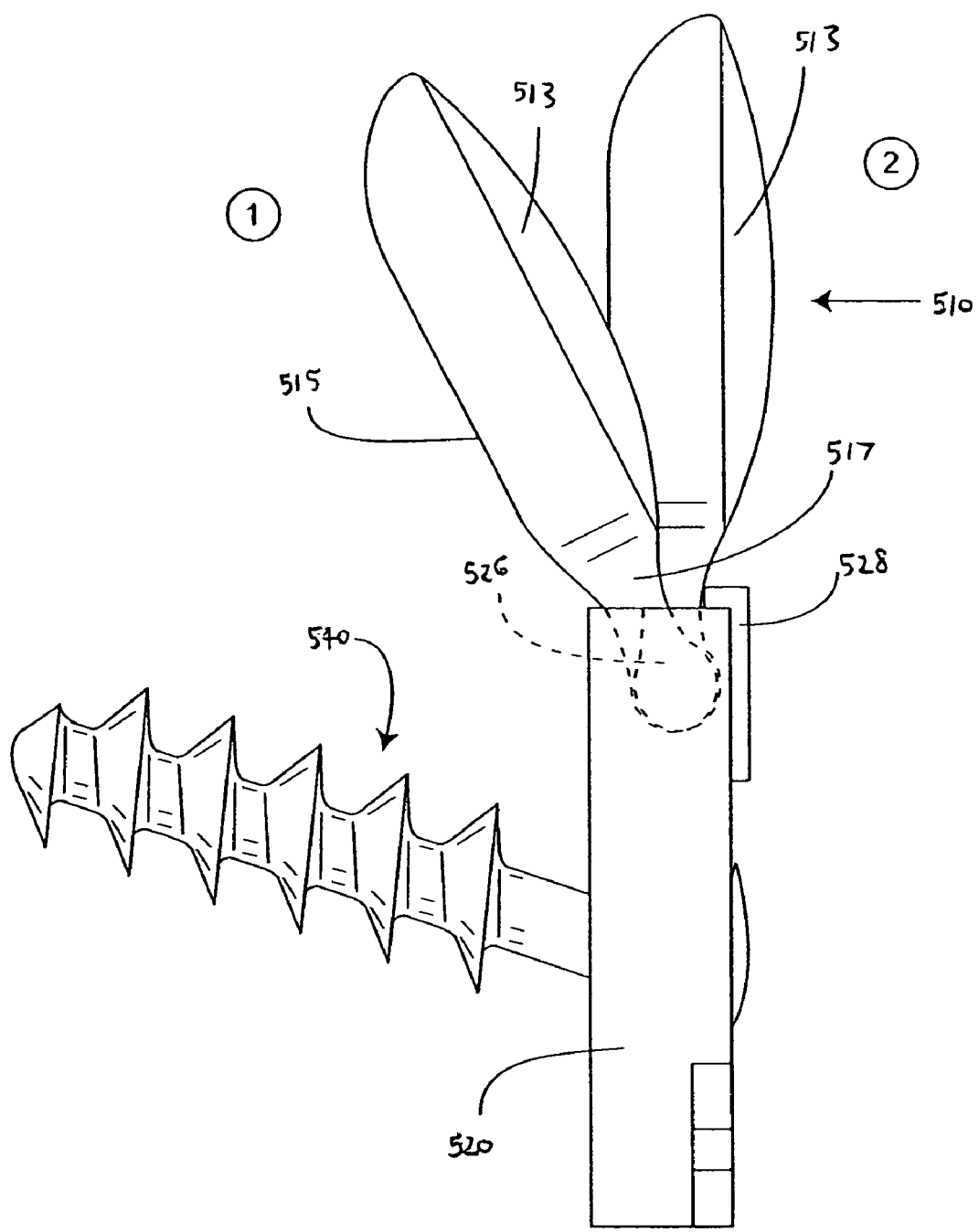

In a preferred embodiment, the spheroidal joint arrangement 538 includes a spherical pivot end 526 and a cavity 527 having a shape approximately conforming to the spherical pivot end 526 so that the spheroidal joint arrangement 538 is a ball-in-socket arrangement. The ball-in-socket arrangement 538 allows the intervertebral plate 510 to move relative to the anchoring plate 520. For example, as shown in FIG. 11A the intervertebral plate 510 can tilt in a posterior direction (to position 1, for example) and can tilt in an anterior direction (to position 2, for example). As the intervertebral plate 510 tilts in the posterior direction, the isthmus 517 moves within the posterior notch 524 so that the intervertebral plate 510 can continue tilting. Conversely, as the intervertebral plate 510 tilts in a anterior direction (to position 2, for example), the isthmus 517 contacts the plug 528, limiting the amount of tilt of the intervertebral plate 510 in a anterior direction. As seen in FIG. 11A the plug 528 acts like a flange extending from the anchoring plate 520 in order to limit the motion of the intervertebral plate 510 relative to the anchoring plate 520. Thus the intervertebral plate 510 can be about parallel to the anchoring plate 520 to for example retain a fusion plug in place and can rotate counterclockwise in FIG. 11A toward the anchoring plate 520.

Referring to FIG. 11B, the ball-and-socket arrangement allows the intervertebral plate 510 to swivel (to position 3, for example) relative to the anchoring plate 520, potentially providing a physician more freedom to manipulate the implant 500. The amount of swiveling accommodated (and the degree of freedom of movement accommodated in general) depends on the geometries of the components. For example, where the isthmus 517 is sufficiently narrow and long in length, a greater degree of swiveling in combination with tilt can be achieved, or for example where the plug 528 extends over a portion of the intervertebral plate 510, as shown in FIGS. 11A and 11B, the amount of tilt possible in the anterior direction can be limited, thereby resisting expulsion of the bone graft. One of ordinary skill in the art will appreciate that the freedom of movement of the intervertebral plate 510 relative to the anchoring plate 520 is limited substantially or wholly by the geometries of the components, and therefore can be substantially altered to achieve a desired range of movement.

The ball-and-socket arrangement need not include a ball that extends from the intervertebral plate and a socket that is formed in the anchoring plate. For example, the ball of such a joint can extend from a locking or anchoring plate and the socket can be included in the intervertebral plate. Further, while the preferred embodiment has been described as a ball-and-socket arrangement; other arrangements can be employed with varied results. It should not be inferred that embodiments in accordance with the present invention need include a spheroidal shaped end mated with a rounded cavity. The scope of the present invention is not intended to be limited to ball-and-socket arrangements, but rather is intended to encompass all such arrangements that provide a plurality of degrees of freedom of movement and substitutability of components.

Figure 12:
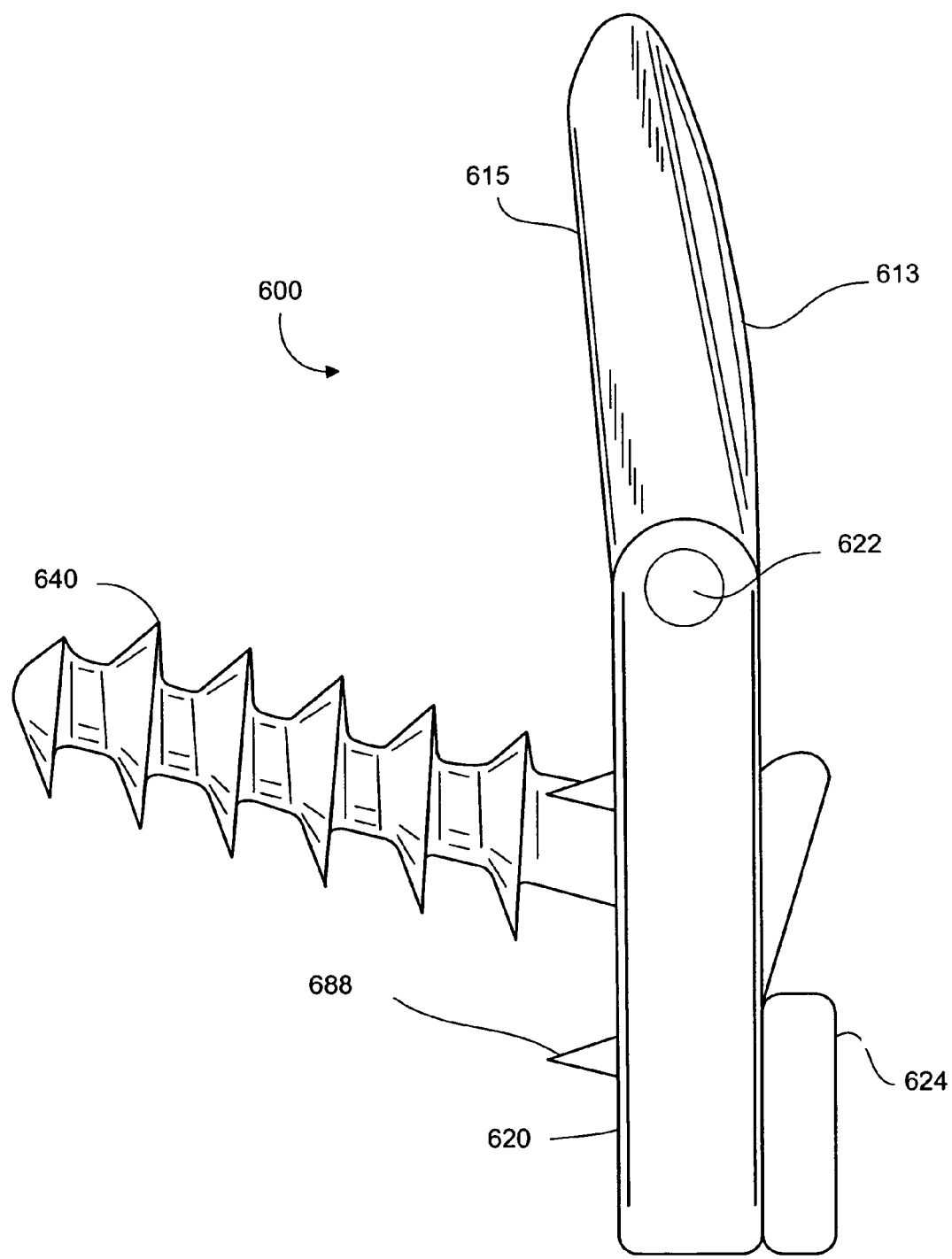
FIG. 12 is a lateral view of still another embodiment of an implant in accordance with the present invention having a bone screw arrangement adapted to have a range of motion and anchoring plate cleats.

Referring to FIG. 12, yet another embodiment of an implant 600 in accordance with the present invention is shown. The implant 600 can further optionally include plate cleats 688 extending from a surface of the anchoring plate 620 substantially contacting the corresponding vertebra. The plate cleats 688 can help anchor the anchoring plate 620 in position either to assist in resisting shifting as a bone screw 640 is associated with the vertebra, or as an adjunct to the bone screw 640. Surface roughening caused by the plate cleats 688 can further promote bone growth near and/or integrally with the anchoring plate 620. As shown particularly in FIG. 12 there are four plate cleats (one behind the other) 688, each plate cleat 688 having a conical structure. However, as above the plate cleats 688 can vary in size, number and shape. For example, the plate cleats 688 can have a saw-tooth shape, a pyramid shape, a curved shape, etc. In FIG. 12, retainer 624 can be used to keep the bone screw 640 from backing out. Retainer 624 can be secured to the anchoring plate 620 with a screw.

It should be noted that with any and all of the embodiments described herein can selectively benefit from some or all of the advantages described herein with regard to every other embodiment described herein.

FIG. 13 is a simplified anterior view of the targeted motion segment 1 of FIGS. 1 and 2 including an embodiment of an implant in accordance with the present invention fixedly associated with the upper vertebra of the targeted motion segment 1. FIG. 14 is a simplified lateral view of the targeted motion and implant of FIG. 13. As described above, the targeted motion segment 1 includes a bone graft 5 comprising a plug positioned within a cavity formed in the unhealthy disc 4 accessed by way of an anterior approach. The bone graft 5 is prevented from being expelled from the cavity as a result of compressive forces applied to the spine or other forces by the intervertebral plate 410, which as seen particularly in FIG. 14 comes in contact or near contact with the bone graft 5. The anchoring plate 410 is fixed to the upper vertebra 2 so that the intervertebral plate 410 extends over the bone graft 5, obstructing movement of the bone graft 5 in an anterior direction. If desired the anchoring plate 420 can instead be affixed to the lower vertebra 3.

Figure 17:
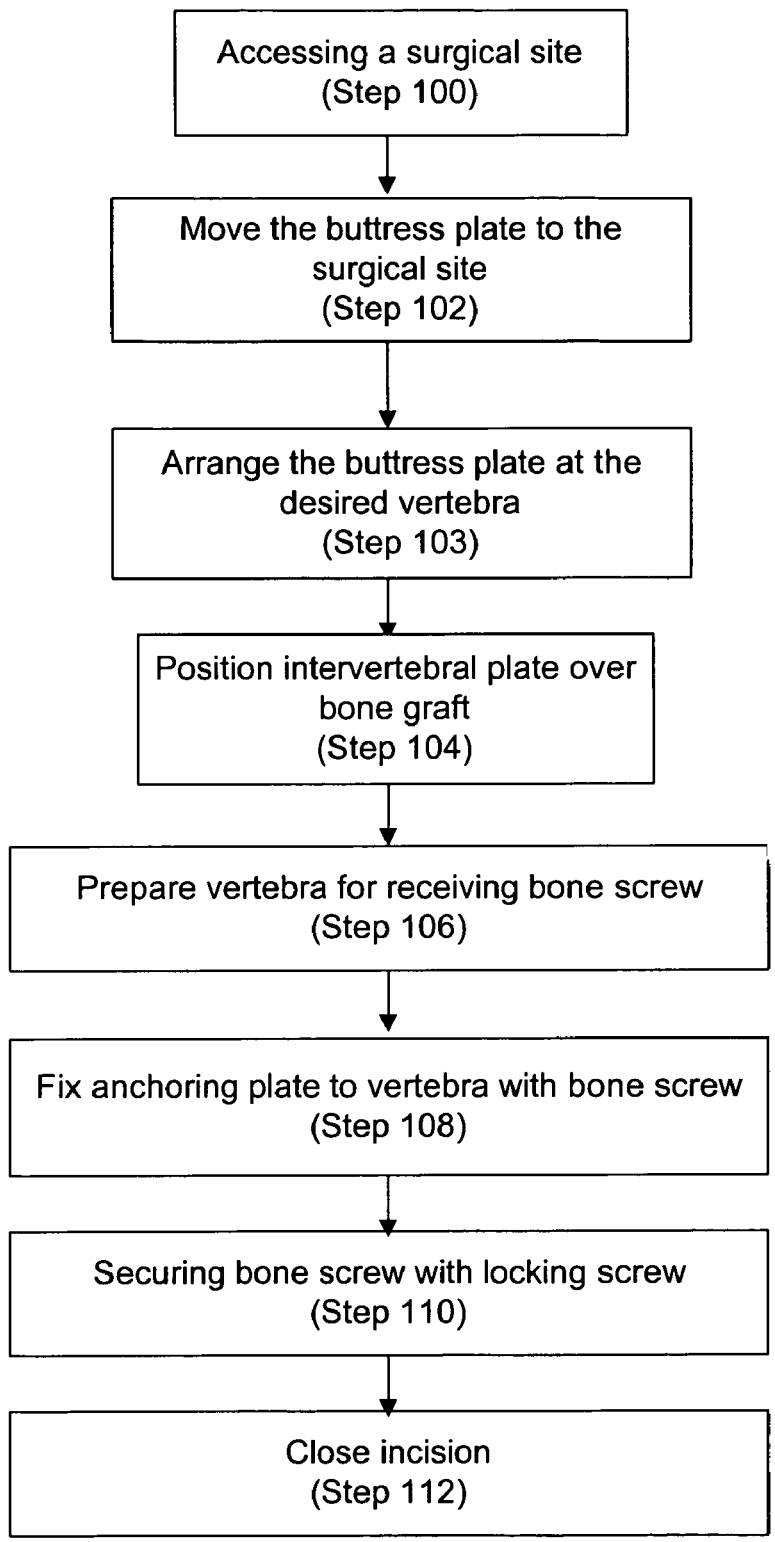
FIG. 17 is a flow diagram of an embodiment of a method for resisting expulsion of a bone graft in accordance with the present invention.

FIG. 17 is a flow chart of an embodiment of a method in accordance with the present invention for implanting an implant as described in FIGS. 2A through 8B. Embodiments of the present invention can be inserted in the following manner, however, only elements of the embodiment 100 will be set forth herein. First an incision is made from an anterior approach (Step 100). Through the incision, instruments are positioned to remove a portion of a disk and replace the removed potion with a fusion plug. The intervertebral plate 110 is urged into the incision (Step 102).

Once the buttress plate 100 is positioned as desired at a corresponding vertebra (Step 103), the intervertebral plate 110 is positioned to obstruct expulsion of the bone graft (Step 104). Once the anchoring plate 120 is positioned, prior to the positioning of the anchoring plate 120, or prior to the positioning of the intervertebral plate 110, a bore can be drilled in the bone to accommodate the bone screw 140 (Step 106). Alternatively the screw 140 can be self-tapping. The bone screw 140 is then threaded and/or inserted through the bore 130 and secured to the bone of the vertebrae, holding the intervertebral plate 110 in place (Step 108). A locking plate 124 can then be positioned over the anchoring plate 120 to lock the bone screw 140 in place and to lock the position of the intervertebral plate 110 and the anchoring plate 120 in place (Step 110). So positioned, a protuberance 126 is disposed at least partially through the bore 130 and in contact or near contact with a head 142 of the bone screw 140 to keep the bone screw 140 from backing out. A keel 128 of the locking plate 124, having a sharp chisel-shaped end, preferably can self-cut a groove in the bone so that the keel 128 is locked into the bone. In some embodiments, the keel 128 is aligned by and received in a groove 131 of the anchoring plate 120. Alternatively, a groove can be pre-cut in the bone to receive the keel 128. A bore 129 of the locking plate 124 aligns with a threaded bore 131 of the anchoring plate 120 and a machine screw can be inserted to fix the locking plate 124 to the anchoring plate 120. Locking prevents the anchoring plate 120 and the intervertebral plate 110 from rotating relative to each other and resists movement relative to the vertebrae. Further, the locking plate 124 prevents the bone screw 140 from backing out from the vertebra. Once the buttress plate 100 is positioned and fixed in place, the incision can be closed (Step 112).

Figure 15A:
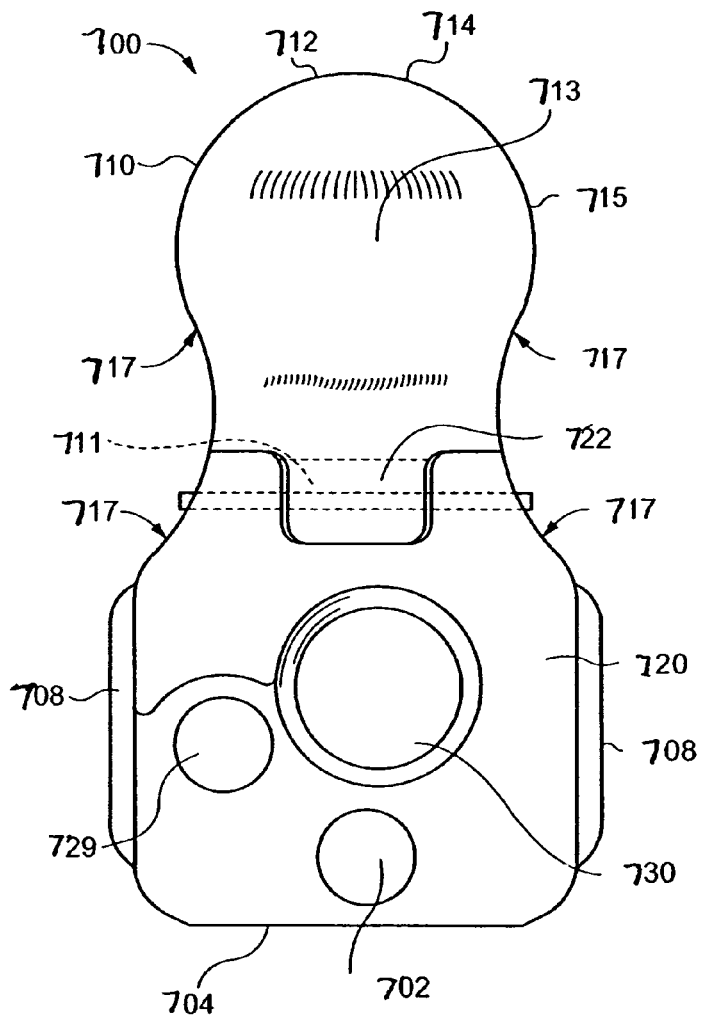
FIGS. 15A and 15B depict yet an alternative embodiment of the invention.
Figure 15B:
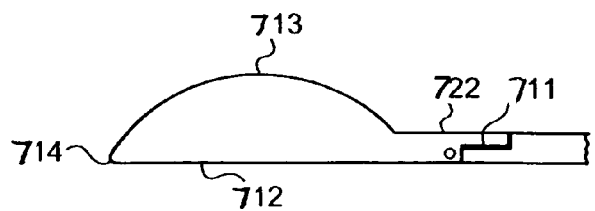

FIG. 15A depicts a posterior view of another embodiment 700 of the implant of the invention. The buttress plate embodiment 700, as well as all of the embodiments herein, can benefit from some or all of the features and advantages with regard to the other embodiments described herein. As shown, the buttress plate 700 has an intervertebral plate 710 that can have a tapered or thinned distal end 712. The intervertebral plate 710 further can be curved so that a superior surface 713 of the intervertebral plate 710 is convex, and an inferior surface 715 is concave. In one embodiment, the inferior surface 715 is substantially flat whereby the superior surface 713 is convex (FIG. 15B). As shown in FIG. 15B, the convex superior surface 713 tapers downward at an increased angle toward the inferior surface 715 at the distal end 712. This contour of the superior surface 713 aids in smooth insertion of the intervertebral plate 710 into the facet joint. As with other embodiments described above, the intervertebral plate 710 also can be made of a flexible, biocompatible material, such as PEEK, to maintain joint mobility and flexibility.

The intervertebral plate 710 is connected flexibly with the anchoring plate 720, preferably with a hinge 722. The hinge 722 allows the intervertebral plate 710 and the anchoring plate 720 of the buttress plate 700 to bend with respect to one another between an extended position and a bent or folded position as discussed above. Once the anchoring plate 720 is positioned adjacent to the bone, preferably the anteriorly on a vertebral body a first bone screw can be inserted through a first bore 730 through the anchoring plate 720 and embedded into the bone of the vertebral body. In addition, once the anchoring plate 720 is secured with the first bone screw, a second bone screw can be inserted through a second bore 729 in the anchoring plate 720, whereby the second bone screw would be embedded into the bone of the vertebral body. Details of the first and second bores are discussed above.

The anchoring plate 720 is made of a biocompatible flexible material, preferably titanium or any other biocompatible flexible material as described herein, for example PEEK, that will support the use of bone screws and other hardware, as described below. The anchoring plate 720 bends downward about the hinge 722 over a wide range of angles relative to the intervertebral plate 710. In another embodiment, any other type of interface between the intervertebral plate 710 and the anchoring plate 720 is contemplated (e.g. ball and socket joint). This flexibility facilitates positioning and insertion of the intervertebral plate 710.

FIG. 15B depicts a side view of the buttress plate and anchoring plate in accordance with one embodiment. As shown in FIG. 15B, the intervertebral plate 710 includes an hyper-extension tab 722 in one embodiment. The hyper-extension tab 722 prevents the intervertebral plate 710 from moving relative to the anchoring plate 720 in a direction beyond the extended position which is shown in FIGS. 15A and 15B. The anchoring plate 720 preferably includes a recess 711 at the interface between the anchoring plate 720 and the intervertebral plate 710 which seats the tab 722 in the extended position which is shown in FIG. 15A. When the intervertebral plate 710 is bent at an angle, the tab 722 is not in contact with the recess 711. However, the tab 722 comes into contact with the recess 711 when in the extended position, as shown in FIG. 15A. Thus, the tab 722, when seated in the recess 711, prevents the intervertebral plate 710 from moving beyond the extended position depicted.

As shown in FIG. 15A, the anchoring plate 720 preferably includes a third bore 702 located near a rear edge, whereby the third bore 752 preferably receives an engaging rod 816 (FIG. 16B) of an implantation tool 800 described below. The third bore 702 preferably extends through the superior and inferior surfaces of the anchoring plate, although not necessarily. Although the third bore 702 is circular in shape, any other shape is contemplated which engages a correspondingly shaped engaging rod 816 (FIG. 16B). The rear edge 704 of the anchoring plate 720 can be engaged by the engagement head 806 (FIG. 16B) of the implantation tool 800 as described below.

In addition, the anchoring plate 720 preferably includes one or more winged protrusions, such as tabs, winglets or ears, 708 which protrude from the side edges of the anchoring plate 720. FIG. 15A illustrates the buttress plate 700 having two winged protrusions 708. The protrusions 708 serve as guides to successfully couple the buttress plate 700 to the implantation tool 800. In addition, the protrusions act as an engaging mechanism which secures the buttress plate 700 to the tool 800. It should be noted that the winged protrusions 708 are preferred and the buttress plate 700 can be configured in any other appropriate design to ensure that the buttress plate 700 is able to be effectively guided and secured to the implantation tool 800.

FIG. 16A depicts an implantation tool in accordance with one embodiment of the present invention. As shown in FIG. 16A, the tool 800 preferably includes a handle 802 having a proximal end and a distal end. The tool 800 includes an actuating switch 808 as well as a shaft 804 extending from the distal end of the handle 802. As shown in FIG. 16A, the shaft 804 preferably extends axially with the handle 802, although the shaft 804 may be at an angle with respect to the handle 802. Extending from the shaft 804 is an engagement head 806, whereby the engagement head is preferably oriented at an angle with respect to the shaft 804 and/or the handle 802. The angle of the head 806 relative to the shaft 804 aids the surgeon in the process of implanting the buttress plate 700 in the spine. Preferably the head is at an angle between 45 and 90 degrees relative to the handle 804. However, other angles are contemplated.

Referring to FIG. 16B, the engagement head 806 preferably has a forked configuration and includes a pair of side walls 810, an engagement seat 812 as well as a receiving space 818 which is defined as the area between the side walls 810 and the seat 812. The engagement head 806 preferably includes a retractable engaging rod 816 which extends partially into the receiving space 818. The side walls 810 each have an inner side which includes a slot 812 whereby the slots 812 face the receiving space 818. The slots 812 are dimensioned to slidably receive the wing protrusions 708 of the lateral mass plate 720 as well as secure the anchoring plate 720 to the engagement head 806. The engagement seat 812 receives the rear edge 704 of the anchoring plate 720.

In one embodiment, the engagement head 806 preferably includes the engaging rod 816, as shown in FIG. 16B. The engaging rod 816 is dimensioned to fit within the third bore 702 in the anchoring plate 720. The engaging rod 816 is coupled the switch 808 on the handle 802, whereby actuation of the switch 808 causes the engaging rod 816 to retract. Upon being retracted, the engaging rod 816 disengages the third bore 702 and allows the buttress plate 700 to be disengaged from the engagement head 806. It is preferred that the tool 800 includes a spring or other urging means to urge the engaging rod 816 to the extended position, as shown in FIG. 16B. In another embodiment, the engaging rod 816 is freely moveable between the extended and retracted positions without a biasing force applied thereto.

It should be noted that the engaging rod 816 is shown as being a circular cylinder in FIGS. 16A and 16B. However, it is contemplated that the engaging rod 816 can have any other shape which conforms to the shape of the third bore 702 in the anchoring plate 720. In another embodiment, the engagement head 806 does not include an engaging rod 816 but some other mechanism to secure the buttress plate 700 to the tool 800. In yet another embodiment, the slots 812 in the side walls 810 can be used to retain the buttress plate 700 in the head 806 without the use of an engaging mechanism.

In preferred operation, to engage the buttress plate 700 with the tool 800, the implant 700 is oriented to be right side up such that the rear surface 704 of the buttress plate 700 will conform and mate with the engagement seat 814. The buttress plate 700 is aligned with the forked portion of the engagement head 806, whereby the winged protrusions 708 of the buttress plate 700 are inserted into the slot openings 812. Upon registering the winged protrusions 708 into the corresponding slots 812, the anchoring plate 720 is guided into engagement by the slots 812 until the rear edge 704 mates with the engagement seat 814. Preferably the engaging rod 816 is then inserted into the third bore 702, thereby securing the anchoring plate 720 to the engagement head 806. In one embodiment, the user manually actuates the switch 808 to retract the engaging rod 816 to allow the anchoring plate 720 to be inserted completely in the receiving space. The switch 808 is then manually released when the bore 702 and engaging rod 816 are aligned such that the engaging rod 816 then extends and engages the third bore 702. In another embodiment, contact between the superior surface of the anchoring plate 720 and the engaging rod 816 causes the engaging rod 816 to slightly retract while the anchoring plate 720 is moved into the engagement seat 814. Once the anchoring plate 720 is seated, the third bore 702 preferably registers with the engaging rod 816, whereby the urging force causes the engaging rod 816 to automatically engage the third bore 702.

During the surgical procedure, the intervertebral plate 710 is positioned over the bone plug or fusion cage as described in detail above. Upon the intervertebral plate 710 being satisfactorily positioned and the anchoring plate is screwed in place, the surgeon preferably actuates the switch 808 to disengage the engaging rod 816 from the third bore 702. The surgeon then draws the tool 800 away from the spine, whereby the anchoring plate 720 slides out of the received area and is guided by the slots 812. The anchoring plate 720 is then anchored into the vertebral body as discussed above.

Materials for Use in Implants of the Present Invention

In some embodiments, the implant, and components of the implant (i.e., a anchoring plate, a bone screw, a locking screw, etc.) can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof (in particular an intervertebral plate) can also be fabricated from somewhat flexible and/or deflectable material. In such embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate7, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

The foregoing description of the present invention has been presented for purposes of illustration and description. It is not intended to be exhaustive or to limit the invention to the precise forms disclosed. Many modifications and variations will be apparent to practitioners skilled in this art. The embodiments were chosen and described in order to explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. A method for retaining a fusion plug in place in the disk space between adjacent vertebrae, the method including:
    selecting a buttress plate having an anchoring plate and an intervertebral plate with the intervertebral plate connected to the anchoring plate;
    positioning the anchoring plate relative to a vertebra and the intervertebral plate relative to the fusion plug;
    anchoring the anchoring plate to the vertebra with the intervertebral plate positioned over the fusion plug so that the fusion plug can not be expelled from between the disk space; and
    securing a locking plate to the anchoring plate so that a keel extending from the locking plate penetrates the vertebra and prevents rotation of the buttress plate relative to the vertebra.

2. The method of claim 1 wherein the positioning step included pivoting the intervertebral plate relative to the anchoring plate.

3. The method of claim 1 wherein the anchoring step includes using a screw to anchor the anchoring plate to the vertebra and securing the locking plate includes positioning a protuberance of the locking plate in a bore of the anchoring plate that receives the screw to prevent back out of the screw from the anchoring plate and positioning the keel in a groove along an edge of the anchoring plate.

4. The method of claim 3 including using a machine screw to lock the locking plate to the anchoring plate.

5. The method of claim 1 including the anchoring plate having protrusions and the step of using the protrusions to fix to position of the anchoring plate relative to the vertebra.

6. A method for retaining a fusion plug in place in the disk space between adjacent vertebrae, the method including:
   selecting a buttress plate having an anchoring plate and an intervertebral plate with the intervertebral plate hinged to the anchoring plate;
   positioning the anchoring plate relative to a vertebra and the intervertebral plate relative to the fusion plug;
   anchoring the anchoring plate to the vertebra with the intervertebral plate positioned over the fusion plug so that the fusion plug can not be expelled from between the disk space; and
   securing a locking plate to the anchoring plate 'so that a keel extending from the locking plate penetrates the vertebra and prevents rotation of the buttress plate relative to the vertebra.

7. The method of claim 6 wherein the positioning step included pivoting the intervertebral plate relative to the anchoring plate.

8. The method of claim 6 wherein the anchoring step includes using a screw to anchor the anchoring plate to the vertebra and securing the locking plate includes positioning a protuberance of the locking plate in a bore of the anchoring plate that receives the screw to prevent back out of the screw from the anchoring plate and positioning the keel in a groove along an edge of the anchoring plate.

9. The method of claim 8 including using a machine screw to lock the locking plate to the anchoring plate.

10. The method of claim 6 including the anchoring plate having protrusions and the step of using the protrusions to fix to position of the anchoring plate relative to the vertebra.

11. A buttress plate to resist expulsion of a bone graft from between two vertebrae, the buttress plate comprising:
   an anchoring plate adapted to he fixedly associated with one of the two vertebrae, the anchoring plate including a bore;
   an intervertebral plate connected with the anchoring plate, the intervertebral plate being adapted to extend across at least a portion of an intervertebral space between the two vertebrae, wherein the intervertebral plate is pivotable relative to the anchoring plate;
   a bone screw received through the bore of the anchoring plate; and
   a locking plate mated with the anchoring plate in overlapping relation with the bone screw to prevent back out of the bone screw from the bore of the anchoring plate, wherein the locking plate is further configured to penetrate the one of the two vertebra to prevent rotation of the buttress plate relative to the one of the two vertebrae.

12. The buttress plate of claim 11, wherein the intervertebral plate is pivotably connected with the anchoring plate by one of a hinge and a ball-in-socket arrangement.

13. The buttress plate of claim 11, further comprising:
   a locking screw adapted to block the bone screw from at least one of a backward displacement and a rotational displacement.

14. The buttress plate of claim 13, wherein:
   the locking screw includes a chisel-point end; and
   the chisel point end self-cuts the locking screw into the vertebra.

15. The buttress plate of claim 11, wherein the locking plate includes:
   a first locking screw bore;
   a keel;
   a protuberance;
   wherein the anchoring plate includes a second locking screw bore adapted to align with the first locking screw bore of the locking plate for receipt of a locking screw to secure the locking plate to the anchoring plate with the keel received in a groove along an edge of the anchoring plate; and
   wherein the protuberance is adapted to be received at least partially within the bore of the anchoring plate to prevent back out of the bone screw.

* * * * *